United States Patent
Taylor

(10) Patent No.: US 11,259,737 B2
(45) Date of Patent: Mar. 1, 2022

(54) SYSTEMS AND METHODS FOR PERFORMING NEUROPHYSIOLOGIC MONITORING DURING SPINE SURGERY

(71) Applicant: NuVasive, Inc., San Diego, CA (US)

(72) Inventor: William Taylor, Del Mar, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/073,772

(22) Filed: Nov. 6, 2013

(65) Prior Publication Data

US 2015/0088030 A1 Mar. 26, 2015

Related U.S. Application Data

(60) Provisional application No. 61/722,923, filed on Nov. 6, 2012.

(51) Int. Cl.
| | |
|---|---|
| *A61B 5/389* | (2021.01) |
| *A61B 17/02* | (2006.01) |
| *A61B 5/296* | (2021.01) |
| *A61B 17/00* | (2006.01) |

(Continued)

(52) U.S. Cl.
CPC .............. *A61B 5/389* (2021.01); *A61B 5/296* (2021.01); *A61B 5/407* (2013.01); *A61B 5/4041* (2013.01); *A61B 5/4893* (2013.01); *A61B 17/02* (2013.01); *A61B 17/0206* (2013.01); *A61B 5/743* (2013.01); *A61B 2017/00039* (2013.01); *A61B 2017/00115* (2013.01); *A61B 2017/00199* (2013.01); *A61B 2017/00225* (2013.01); *A61B 2017/00929* (2013.01); *A61B 2017/0256* (2013.01);

(Continued)

(58) Field of Classification Search
CPC .......................... A61B 5/04001; A61B 5/0488; A61N 1/0456; A61N 1/08; A61N 1/36014; A61N 1/36003; A61N 1/36021–36028
USPC .......................... 600/554; 607/46, 48, 49, 62
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |

(Continued)

FOREIGN PATENT DOCUMENTS

| | | |
|---|---|---|
| CN | 101930947 | 12/2010 |
| JP | 2006512983 A | 4/2006 |

(Continued)

OTHER PUBLICATIONS

"Electromyography System," International Search Report from International Application No. PCT/US00/32329, dated Apr. 27, 2001, 9 pages.

(Continued)

*Primary Examiner* — Rene T Towa

(57) ABSTRACT

A neuromonitoring system utilizes transcutaneous, transabdominal nerve root stimulation to monitor the health and status of the motor neural pathways of the lower extremities during the portions of a surgical procedure in which a tissue retraction assembly is used to maintain an operative corridor. A method of monitoring the status of nerve during a spinal surgical procedure delivers a transcutaneous, transabdominal stimulation signal to the spine. A determination is made of a stimulation threshold required to elicit a neuromuscular response from the stimulation signal.

17 Claims, 17 Drawing Sheets

(51) Int. Cl.
*A61B 5/00* (2006.01)
*A61B 90/00* (2016.01)
(52) U.S. Cl.
CPC .............. *A61B 2017/0262* (2013.01); *A61B 2090/0814* (2016.02); *A61B 2505/05* (2013.01)

(56) References Cited

U.S. PATENT DOCUMENTS

| | | |
|---|---|---|
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Coyler |
| 3,785,368 A | 1/1974 | McCarthy et al. |
| 3,830,226 A | 8/1974 | Staub |
| 3,851,641 A | 12/1974 | Toole et al. |
| 3,957,036 A | 5/1976 | Norman |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,627,441 A * | 12/1986 | Martin ................. A61B 5/0428 128/901 |
| 4,633,889 A | 1/1987 | Talalla et al. |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Brass et al. |
| 5,196,015 A | 3/1993 | Neubardt |
| 5,220,920 A | 6/1993 | Gharib |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,389,069 A | 2/1995 | Weaver |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,599,279 A | 2/1997 | Slotman |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,758,643 A | 6/1998 | Wong et al. |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,797,854 A | 8/1998 | Hedgecock |
| 5,806,522 A | 9/1998 | Katims |
| 5,807,272 A | 9/1998 | Kun et al. |
| 5,814,073 A | 9/1998 | Bonutti |
| 5,830,151 A | 11/1998 | Hadzic et al. |
| 5,851,191 A | 12/1998 | Gozani et al. |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,928,159 A | 7/1999 | Eggers et al. |
| 5,935,131 A | 8/1999 | Bonutti |
| 5,938,688 A | 8/1999 | Schiff |
| 5,947,964 A | 9/1999 | Eggers et al. |
| 5,976,094 A | 11/1999 | Gozani |
| 6,004,262 A | 12/1999 | Putz et al. |
| 6,011,985 A | 1/2000 | Athan |
| 6,026,323 A | 2/2000 | Skladnev et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Turner et al. |
| 6,139,493 A | 10/2000 | Koros et al. |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,337,994 B1 | 1/2002 | Stoianovici et al. |
| 6,393,325 B1 | 5/2002 | Mann et al. |
| 6,407,335 B1 | 6/2002 | Franklin-Lees et al. |
| 6,425,859 B1 | 7/2002 | Foley et al. |
| 6,425,901 B1 | 7/2002 | Zhu et al. |
| 6,451,015 B1 | 9/2002 | Rittman et al. |
| 6,466,817 B1 | 10/2002 | Kania et al. |
| 6,500,128 B2 | 12/2002 | Marino |

(56) References Cited

U.S. PATENT DOCUMENTS

| | | | |
|---|---|---|---|
| 6,535,759 B1 | 3/2003 | Epstein et al. | |
| 6,564,078 B1 | 5/2003 | Marino et al. | |
| 6,579,244 B2 | 6/2003 | Goodwin | |
| 6,593,528 B2 | 7/2003 | Franklin-Lees et al. | |
| 6,719,692 B2 | 4/2004 | Kleffner et al. | |
| 6,760,616 B2 | 7/2004 | Hoey et al. | |
| 6,796,985 B2 | 9/2004 | Bolger et al. | |
| 6,819,956 B2 | 11/2004 | DiLorenzo | |
| 6,829,508 B2 | 12/2004 | Schulman et al. | |
| 6,849,047 B2 | 2/2005 | Goodwin | |
| 6,855,105 B2 | 2/2005 | Jackson, III | |
| 6,902,569 B2 | 6/2005 | Parmer et al. | |
| 6,926,728 B2 | 8/2005 | Zucherman et al. | |
| 6,929,606 B2 | 8/2005 | Ritland | |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| D533,875 S | 12/2006 | Miles et al. | |
| 7,177,677 B2 | 2/2007 | Kania et al. | |
| 7,207,949 B2 | 4/2007 | Miles et al. | |
| 7,255,680 B1 | 8/2007 | Gharib | |
| 7,470,236 B1 | 12/2008 | Kelleher et al. | |
| 7,522,953 B2 | 4/2009 | Kaula et al. | |
| 7,582,058 B1 | 9/2009 | Miles et al. | |
| 7,657,308 B2 | 2/2010 | Miles et al. | |
| 7,664,544 B2 | 2/2010 | Miles et al. | |
| 7,691,057 B2 | 4/2010 | Miles et al. | |
| 7,706,843 B2 | 4/2010 | Kaplan | |
| 7,819,801 B2 | 10/2010 | Miles et al. | |
| 7,857,813 B2 | 12/2010 | Schmitz et al. | |
| 7,878,981 B2 | 2/2011 | Strother et al. | |
| 7,887,538 B2 | 2/2011 | Bleich et al. | |
| 7,896,815 B2 | 3/2011 | Thrope et al. | |
| 7,905,840 B2 | 3/2011 | Pimenta et al. | |
| 7,938,830 B2 | 5/2011 | Saadat et al. | |
| 7,963,927 B2 | 6/2011 | Kelleher et al. | |
| 8,068,912 B2 | 11/2011 | Kaula et al. | |
| 2001/0039949 A1 | 11/2001 | Loubser | |
| 2001/0056280 A1 | 12/2001 | Underwood et al. | |
| 2002/0007129 A1 | 1/2002 | Marino | |
| 2002/0072686 A1 | 6/2002 | Hoey et al. | |
| 2002/0123780 A1 | 9/2002 | Grill et al. | |
| 2002/0134570 A1 | 9/2002 | Franklin-Lees et al. | |
| 2002/0161415 A1 | 10/2002 | Cohen et al. | |
| 2002/0193843 A1 | 12/2002 | Hill | |
| 2003/0032966 A1 | 2/2003 | Foley et al. | |
| 2003/0105503 A1 | 6/2003 | Marino | |
| 2004/0199084 A1* | 10/2004 | Kelleher | A61B 5/04001 |
| | | | 600/554 |
| 2004/0203490 A1 | 10/2004 | Kaplan | |
| 2004/0225228 A1* | 11/2004 | Ferree | A61B 17/7092 |
| | | | 600/554 |
| 2005/0004593 A1 | 1/2005 | Simonson | |
| 2005/0004623 A1 | 1/2005 | Miles et al. | |
| 2005/0033380 A1 | 2/2005 | Tanner et al. | |
| 2005/0075578 A1 | 4/2005 | Gharib et al. | |
| 2005/0149035 A1 | 7/2005 | Pimenta et al. | |
| 2005/0182454 A1 | 8/2005 | Gharib et al. | |
| 2005/0192575 A1 | 9/2005 | Pacheco | |
| 2006/0025703 A1 | 2/2006 | Miles et al. | |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1 | 1/2007 | Farquhar et al. | |
| 2007/0021682 A1 | 1/2007 | Gharib et al. | |
| 2007/0100212 A1* | 5/2007 | Pimenta | A61B 5/0488 |
| | | | 600/210 |
| 2007/0198062 A1 | 8/2007 | Miles et al. | |
| 2007/0293782 A1 | 12/2007 | Marino | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |
| 2008/0097164 A1 | 4/2008 | Miles et al. | |
| 2008/0167574 A1 | 7/2008 | Farquhar et al. | |
| 2008/0221473 A1 | 9/2008 | Calancie et al. | |
| 2009/0018399 A1 | 1/2009 | Martinelli | |
| 2009/0018610 A1 | 1/2009 | Gharib et al. | |
| 2009/0054804 A1* | 2/2009 | Gharib | A61B 5/0488 |
| | | | 600/554 |
| 2009/0105604 A1 | 4/2009 | Bertagnoli et al. | |
| 2009/0124860 A1 | 5/2009 | Miles et al. | |
| 2009/0177112 A1 | 7/2009 | Gharib et al. | |
| 2009/0192403 A1 | 7/2009 | Gharib et al. | |
| 2009/0204016 A1 | 8/2009 | Gharib et al. | |
| 2009/0204176 A1 | 8/2009 | Miles et al. | |
| 2009/0209879 A1 | 8/2009 | Kania et al. | |
| 2009/0259108 A1 | 10/2009 | Miles et al. | |
| 2010/0010367 A1 | 1/2010 | Foley et al. | |
| 2010/0036384 A1 | 2/2010 | Gorek et al. | |
| 2010/0069783 A1 | 3/2010 | Miles et al. | |
| 2010/0076335 A1 | 3/2010 | Gharib et al. | |
| 2010/0094093 A1 | 4/2010 | Miles et al. | |
| 2010/0105986 A1 | 4/2010 | Miles et al. | |
| 2010/0105987 A1 | 4/2010 | Miles et al. | |
| 2010/0113884 A1 | 5/2010 | Miles et al. | |
| 2010/0130827 A1 | 5/2010 | Pimenta et al. | |
| 2010/0137690 A1 | 6/2010 | Miles et al. | |
| 2010/0152603 A1 | 6/2010 | Miles et al. | |
| 2010/0152604 A1 | 6/2010 | Kaula et al. | |
| 2010/0160738 A1 | 6/2010 | Miles et al. | |
| 2010/0174146 A1 | 7/2010 | Miles et al. | |
| 2010/0174147 A1 | 7/2010 | Miles et al. | |
| 2010/0174148 A1 | 7/2010 | Miles et al. | |
| 2010/0249644 A1 | 9/2010 | Miles et al. | |
| 2010/0273738 A1 | 10/2010 | Valcke et al. | |
| 2010/0286554 A1* | 11/2010 | Davis | A61B 5/24 |
| | | | 600/554 |
| 2010/0286784 A1 | 11/2010 | Curran et al. | |
| 2010/0312103 A1 | 12/2010 | Gorek et al. | |
| 2012/0109233 A1 | 5/2012 | Lee | |
| 2012/0226186 A1* | 9/2012 | Baars et al. | 600/554 |
| 2012/0259156 A1 | 10/2012 | Freeman | |
| 2014/0316484 A1* | 10/2014 | Edgerton et al. | 607/46 |
| 2015/0088030 A1 | 3/2015 | Taylor | |
| 2015/0230749 A1* | 8/2015 | Gharib | A61B 5/4566 |
| | | | 600/546 |

FOREIGN PATENT DOCUMENTS

| | | |
|---|---|---|
| JP | 2012505707 A | 3/2012 |
| JP | 2012526614 A | 11/2012 |
| WO | 2008/124079 A1 | 10/2008 |
| WO | 2008124079 | 10/2008 |
| WO | 2010/044880 A1 | 4/2010 |
| WO | 2010044880 | 4/2010 |
| WO | WO 2013/071309 | 5/2013 |

OTHER PUBLICATIONS

"Nerve Proximity and Status Detection System and Method," International Search Report from International Application No. PCT/US01/18606, dated Oct. 18, 2001, 6 pages.

"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Percutaneous Pedicle Integrity Assessments," International Search Report from International Application No. PCT/US02/35047, dated Aug. 11, 2003, 5 pages.

"Systems and Methods for Performing Surgery Procedures and Assessments," International Search Report from International Application No. PCT/US02/30617, dated Jun. 5, 2003, 4 pages.

(56) References Cited

OTHER PUBLICATIONS

"Systems and Methods for Performing Neurophysiologic Assessments During Spine Surgery," International Search Report from International Application No. PCT/US06/03966, dated Oct. 23, 2006, 5 pages.

"Multi-Channel Stimulation Threshold Detection Algorithm for Use in Neurophysiology Monitoring," International Search Report from International Application No. PCT/US06/37013, dated Mar. 19, 2007, 6 pages.

"Neurophysiologic Monitoring System," International Search Report and the Written Opinion from International Application No. PCT/US08/04427, dated Jul. 28, 2008, 6 pages.

"Systems and Methods for Performing Neurophysiologic Monitoring During Spine Surgery," International Search Report and Written Opinion from International Application No. PCT/US14/64449, dated Feb. 2, 2015, 8 pages.

"Neurovision SE Nerve Locator/Monitor," RLN Systems Inc. Operator's Manual, 1999, 22 pages.

Calancie et al., "Stimulus-Evoked EMG Monitoring During Transpedicular Lumbosacral Spine Instrumentation," *Spine*, 1994, 19(24): 2780-2786.

Holland et al., "Higher Electrical Stimulus Intensities are Required to Activate Chronically Compressed Nerve Roots. Implications for Intraoperative Electromyographic Pedicle Screw Testing," *Spine*, 1998, 23(2): 224-227.

Ladenbauer et al., "Stimulation of the Human Lumbar Spinal Cord With Implanted and Surface Electrodes: A Computer Simulation Study," (2010) *IEEE Transactions* 18(6): 637-645.

Minassian et al., "Human lumbar cord circuitries can be activated by extrinsic tonic input to generate locomotor-like activity," (2007) *Human Movement Science* 26(2): 275-295.

Minassian et al., "Neuromodulation of lower limb motor control in restorative neurology," (2012) *Clinical Neurology and Neurosurgery* 114:489-497.

Minassian et al., "Posterior Root-Muscle Reflexes Elicited by Transcutaneous Stimulation of the Human Lumbosacral Cord", (2007) *Muscle Nerve* 35:327-336.

Swash and Snooks, "Slowed motor conduction in lumbosacral nerve roots in cauda equina lesions: a new diagnostic technique,", (1986) *J Neurol Neurosurg Psychiatry* 49:808-816.

Gonzalez et al., "Intraoperative Neurophysiological Monitoring during Spine Surgery: A Review," *Neurosurg Focus*. (2009) 27(4):E6.

Deletis et al., "Intraoperative neurophysiological monitoring of the spinal cord during spinal cord and spine surgery: A review focus on the corticospinal tracts", Clinical Neurophsiology, Elsevier Science, vol. 119, No. 2, pp. 248-264, Dec. 22, 2007.

Gregoire Courtine et al. Modulation of multisegmental monosynaptic responses in a variety of leg muscles during walking and running in humans, The Journal of Physiology, 2007, vol. 582, Edition 3, pp. 1125-1139.

* cited by examiner

SYSTEMS AND METHODS FOR PERFORMING NEUROPHYSIOLOGIC MONITORING DURING SPINE SURGERY

CROSS-REFERENCES TO RELATED APPLICATIONS

This non-provisional application claims priority under 35 U.S.C. 119(e) from U.S. Provisional Application Ser. No. 61/722,923 filed Nov. 6, 2012, the complete disclosure of which is hereby incorporated by reference into this application as if set forth fully herein. The present application incorporates by reference commonly owned and International Patent Application No. PCT/US01/01489, filed Aug. 8, 2011 and entitled "Surgical Access System and Related Methods," and commonly owned U.S. Pat. No. 8,255,045, issued Aug. 28, 2012 and entitled "Neurophysiology Monitoring System," the entire contents of each of which are hereby incorporated by reference into this disclosure as if set forth fully herein.

FIELD

This disclosure relates to a surgical retraction system and related instrumentation and methods for accessing and maintaining a surgical target site for the purpose of performing surgical procedures.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra and the like. Patients that suffer from such conditions usually experience extreme and debilitating pain, as well as diminished nerve function.

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques are gaining favor due to the fact that they involve accessing the surgical target site via incisions of substantially smaller size with greatly reduced tissue displacement requirements. This, in turn, reduces the pain, morbidity, and cost associated with such procedures. One such minimally invasive approach, a lateral trans-psoas approach to the spine, developed by NuVasive®, Inc., San Diego, Calif. (XLIF®) has demonstrated great success in reducing patient morbidity, shortening the duration of hospitalization, and speeding recovery time if it is employed.

To create the lateral access corridor to the lumbar spine, the patient is positioned on his or her side and a surgical access system is advanced through an incision, into the retroperitoneal space, and then through the psoas muscle until the target spinal site (for example, a disc space between a pair of adjacent vertebral bodies) is reached. The surgical access system may include a sequential dilation assembly of increasing diameter and a tissue retraction assembly. The sequential dilation assembly is advanced to the target site first and the retractor assembly is then advanced to the target site over the sequential dilation system. Stimulating electrodes may be provided on the distal tip of one or more of the different components of the surgical access system. Nerve monitoring may be performed while advancing one or more components of the dilation and retraction assemblies to the target site to detect the presence of, and thereby avoid, nerves lying in the trans-psoas path to the target site.

Once the retractor assembly has been docked at a target site however, a nerve may become compromised due to a variety of factors including, but not limited to, compression of the nerve due to inadvertent contact with the retractor blade and patient positioning on the surgical table. Stimulating within the surgical site provides information regarding the health and status of nearby nerves within the surgical site during maintenance of a lateral access corridor. However, the portion of a nerve that is compressed or otherwise affected might not lie within the surgical site such that information regarding the health and status of a greater portion of the motor neural pathway is desirable. Other methods of stimulating the motor neural pathway (e.g., transcranial electric motor evoked potential (MEP) monitoring) use high stimulus intensities and depolarize all nerves along the corticospinal pathway and result in muscle activity of many muscles of the head, upper extremities, torso, and lower extremities sometimes leading to large amounts of patient movement during the procedure. It is generally preferable to conduct nerve monitoring with the least amount of stimulation intensity (and patient movement) as possible necessary (and patient movement) resulting in often excessive patient movement due to contraction of many or all muscles of the head, upper extremities, abdomen, and lower extremities. Furthermore, information regarding each specific nerve root is also desirable because it provides specific information regarding the health and/or status of each nerve root comprising the lumbar plexus. Therefore, a need exists for methods of performing nerve monitoring on a greater portion of the motor neural pathway with the lower amounts of stimulation and greater specificity of the at-risk nerve roots.

SUMMARY

The present disclosure accomplishes this goal by providing novel methods and systems to evaluate the health and status of the lower motor neural pathway before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present disclosure is suitable for use in any number of additional surgical procedures wherein tissue having significant neural structures must be passed through (or near) in order to establish an operative corridor.

According to another broad aspect of the present disclosure, there is provided an access system comprising a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire and one or more dilators (e.g., sequentially dilating cannulae) for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that does not impinge upon the region of the exiting nerve roots. In one optional aspect of the present disclosure, the cephalad-most and/or caudal-most blades may pivot or rotate outward from a central axis of insertion, such that the operative corridor may be further expanded. In a further optional aspect of the present disclosure, the retractor may include a locking element to maintain the blades in an initial alignment during insertion, and a variable-stop mechanism to allow the user to control the degree of expansion of the operative corridor. A blade expander tool may be provided to facilitate manual pivoting of the retractor blades.

The retractor blades may be optionally dimensioned to receive and direct a locking shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which advantageously forms a protective barrier that prevents the migration of tissue (such as nerve roots) into the operative field and the inadvertent advancement of instruments outside the operative field. In an optional embodiment, the caudal-most and/or cephalad-most blades may be fitted with any number of retractor extenders for extending (laterally or length-wise) the blades, which advantageously forms a protective barrier that prevents the migration of tissue (such as muscle and soft tissue) into the operative field and the inadvertent advancement of instruments outside the operative field.

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

According to another broad aspect of the present disclosure, there is provided a method for performing transcutaneous, trans-abdominal stimulation of nerve roots to provide neurophysiologic information as to the health and status of the motor neural pathways of the lower extremities superior and inferior to a surgical target site.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
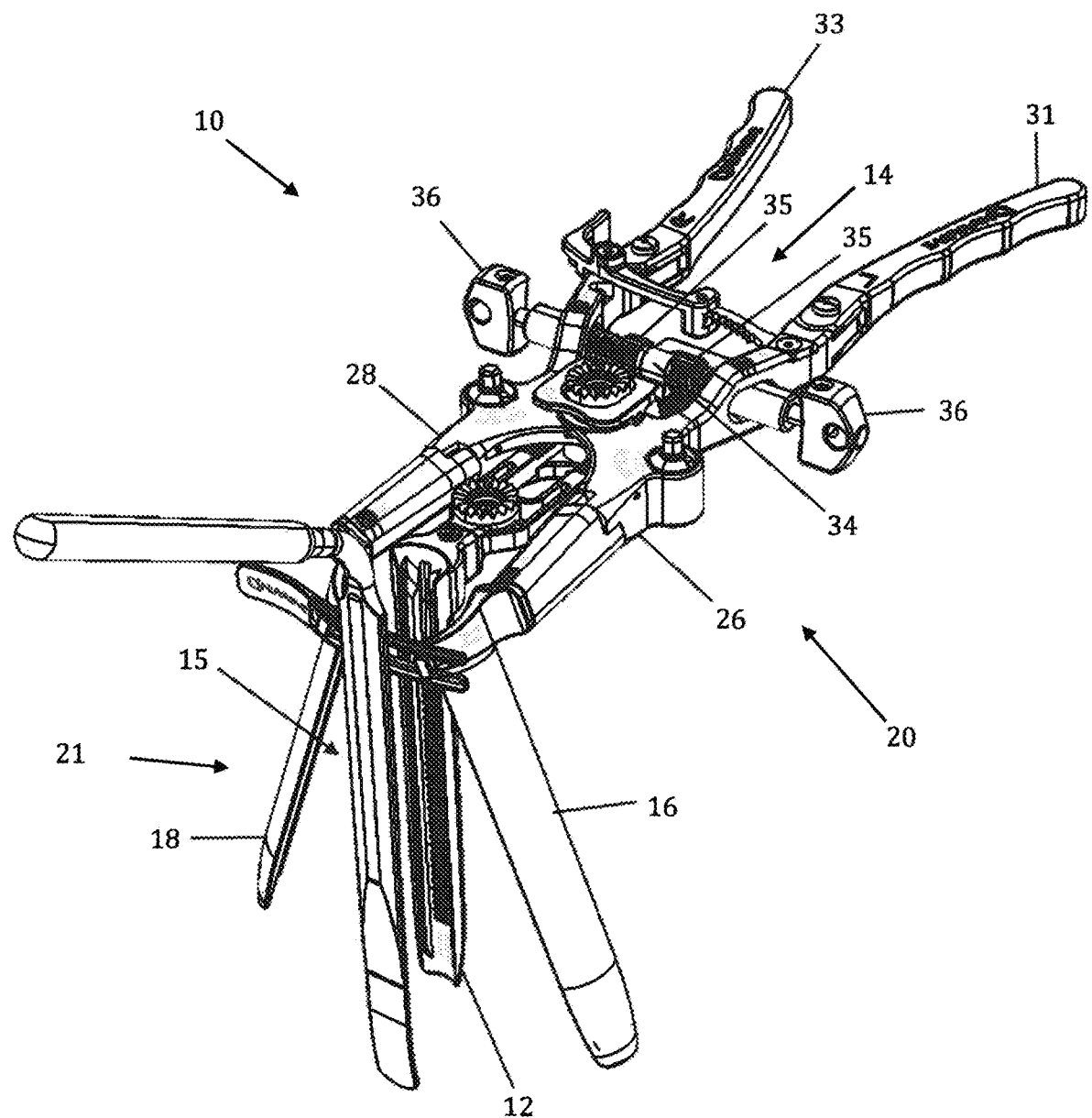
FIG. 1 is a perspective view of one example of a tissue retraction assembly forming part of a surgical access system according to one embodiment of the present disclosure, shown in a fully retracted or "open" position.

Illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present disclosure may be employed in any number of anatomical settings to provide access to any number of different surgical target sites throughout the body. It is also expressly noted that, although shown and described herein largely within the context of lateral surgery in the lumbar spine, the access system of the present disclosure may be employed in any number of other spine surgery access approaches, including but not limited to posterior, postero-lateral, anterior, and antero-lateral access, and may be employed in the lumbar, thoracic and/or cervical spine, all without departing from the present disclosure. The surgical access system disclosed herein boasts a variety of inventive features and components that warrant patent protection, both individually and in combination.

The present disclosure involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present disclosure accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in the above referenced '045 patent. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present disclosure. In so doing, the system as a whole (including the surgical access system of the present disclosure) may be used to form an operative corridor through (or near) any of a variety of tissues having such neural structures, particularly those which, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

Additionally, the neuromonitoring system may perform neuromonitoring as the lateral access corridor is maintained during the surgical procedure. Aspects of the neuromonitoring systems used to facilitate performance of these functions are also described in the following commonly owned patent applications, collectively referred to as the "Neuromonitoring PCT Applications," the entire contents of each of which are hereby incorporated by reference as if set forth fully herein: U.S. Pat. No. 8,068,912, entitled "System and Methods for Determining Nerve Proximity, Direction, and Pathology During Surgery," filed on Jan. 9, 2004; U.S. Pat. No. 7,522,953, entitled "System and Methods for Performing Surgical Procedures and Assessments," filed on Mar. 25, 2004; U.S. Pat. No. 7,905,840, entitled Surgical Access System and Related Methods," filed Oct. 18, 2004; and U.S. Pat. No. 8,255,045, entitled "Neurophysiologic Monitoring System," filed on Apr. 4, 2008, The tissue distraction assembly of the present disclosure, including a plurality of sequential dilators and a k-wire, is employed to distract the tissues extending between the skin of the patient and a given surgical target site (preferably along the posterior region of the target intervertebral disc). Once distracted, the resulting void or distracted region within the patient is of sufficient size to accommodate a tissue retraction assembly of the present disclosure. More specifically, the tissue retraction assembly (comprising a plurality of retractor blades extending from a handle assembly) may be advanced, with the blades in a first generally closed position, over the exterior of the outer dilator. At that point, the handle assembly may be operated to move the retractor blades into a second, open or "retracted" position to create an operative corridor to the surgical target site.

According to one aspect of the disclosure, following (or before) this retraction, a posterior shim element (which is preferably slidably engaged with the posterior retractor blade) may be advanced such that a distal shim extension is positioned within the posterior region of the disc space. If done before retraction, this helps ensure that the posterior retractor blade will not move posteriorly during the retraction process, even though the other retractor blades (e.g. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (e.g. nerves, vasculature, etc.) into or out of the operative corridor. Optionally, the cephalad-most and/or caudal-most retractor blades may be pivoted in an outward direction to further expand the operative corridor. Once the operative corridor is established, any of a variety of surgical instruments, devices, or implants may be passed through and/or manipulated within the operative corridor depending upon the given surgical procedure.

Figure 2:
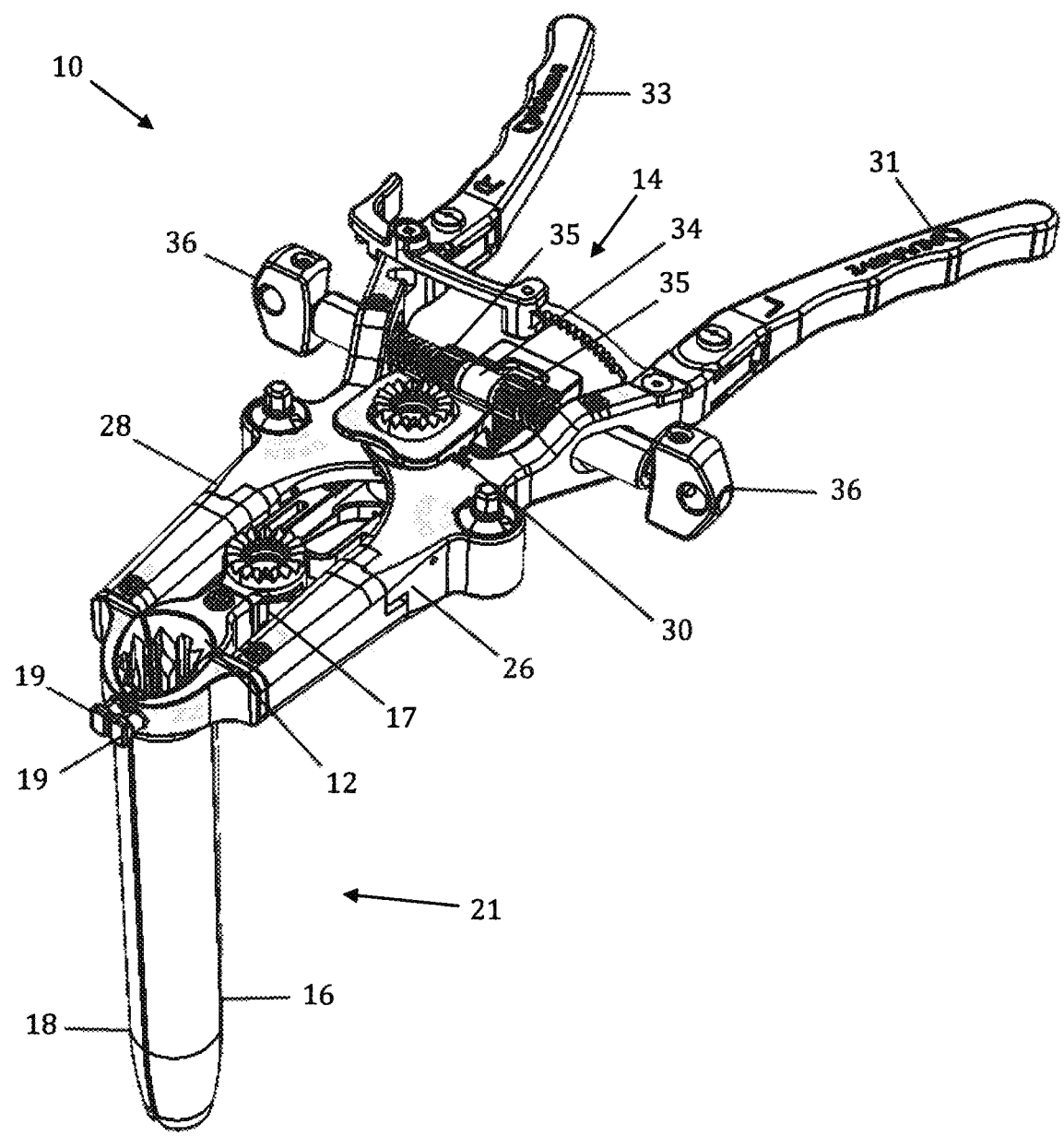
FIG. 2 is a perspective view of the tissue retraction assembly of FIG. 1 shown in a fully closed position.
Figure 3:
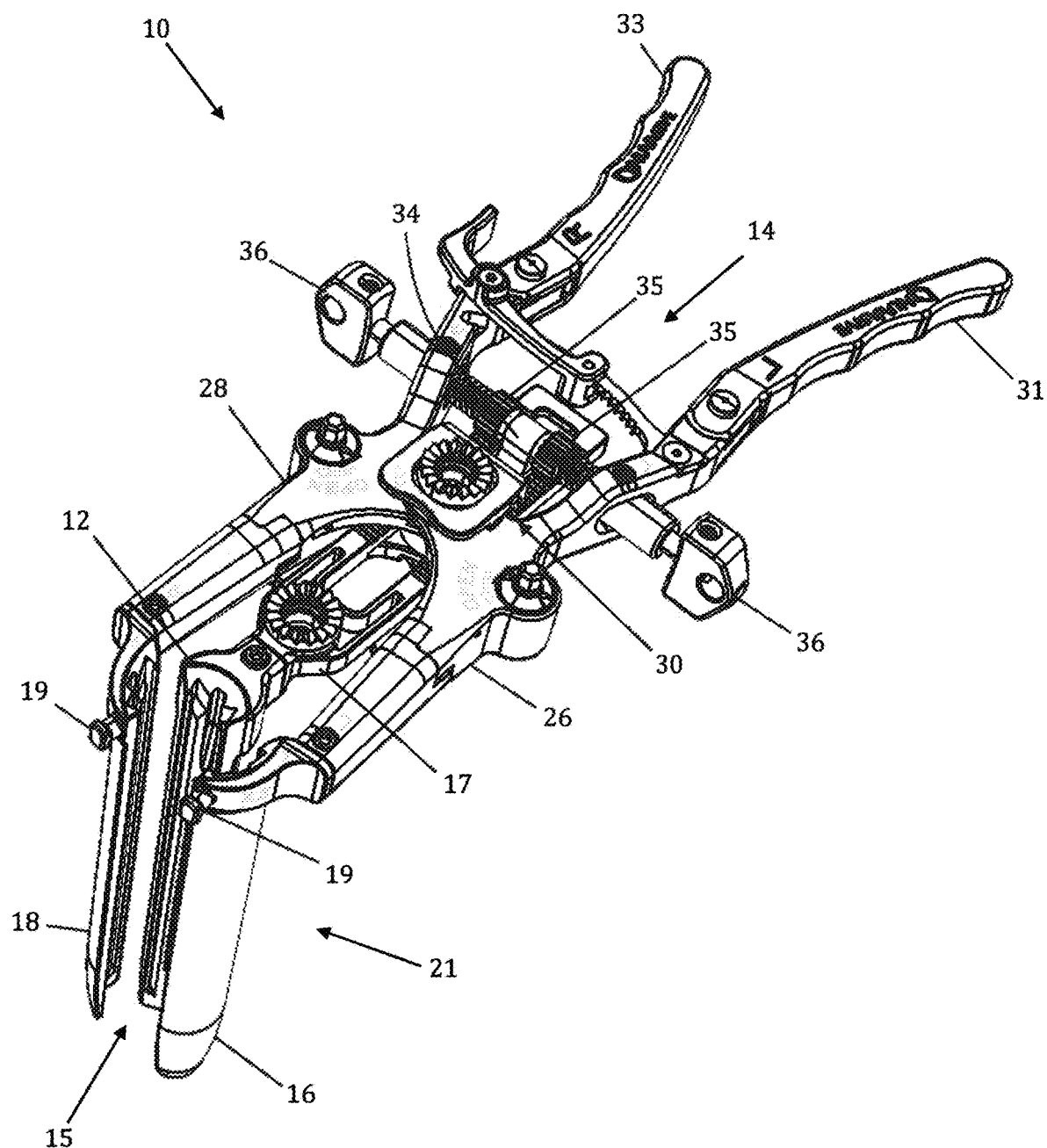
FIG. 3 is a perspective view of the tissue retraction assembly of FIG. 1 shown in a partially open position according to the present disclosure.

FIGS. 1-3 illustrate a tissue retraction assembly 10 forming part of a surgical access system according to the present disclosure, including a plurality of retractor blades 12, 16, 18 extending from a handle assembly 20. By way of example only, the handle assembly 20 is provided with a first retractor blade 12, a second retractor blade 16, and a third retractor blade 18. FIG. 1 illustrates the tissue retraction assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In an important aspect of the present disclosure, the blades 16, 18 are capable of being pivoted or rotated relative to the handle 20, as best appreciated with combined reference to FIGS. 1 & 2. FIG. 2 shows the tissue retraction assembly 10 in an initial "closed" configuration, with the retractor blades 12, 16, 18 generally abutting one another. FIG. 3 shows the tissue retraction assembly 10 in a "partially open" configuration. Although shown and described below with regard to the three-fixed-bladed configuration, it is to be readily appreciated that the number of retractor blades may be increased or decreased without departing from the scope of the present disclosure. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the tissue retraction assembly 10 of the present disclosure may find use in any number of different surgical approaches, including generally posterior, generally postero-lateral, generally anterior and generally antero-lateral.

The handle assembly 20 may be coupled to any number of mechanisms for rigidly registering the handle assembly 20 in fixed relation to the operative site, such as through the use of an articulating arm mounted to the operating table (not shown). The handle assembly 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, a generally triangular cross-section, and/or an oval cross-section. Optional light emitting devices (not shown) may be coupled to one or more of the retractor blades 12, 16, 18 to direct light down the operative corridor 15.

The retractor blades 12, 16, 18 may be composed of any material suitable for introduction into the human body, including but not limited to aluminum, titanium, and/or clear polycarbonate, that would ensure rigidity during tissue distraction. The retractor blades 12, 16, 18 may be optionally coated with a carbon fiber reinforced coating to increase strength and durability. The retractor blades 12, 16, 18 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc.). The retractor blades 12, 16, 18 may be provided in any number of suitable lengths, depending upon the anatomical environment and surgical approach, such as (for example) the range from 20 mm to 150 mm. Based on this range of sizes, the tissue retraction assembly 10 of the present disclosure is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the handle assembly 20 as will be described herein.

Figure 4:
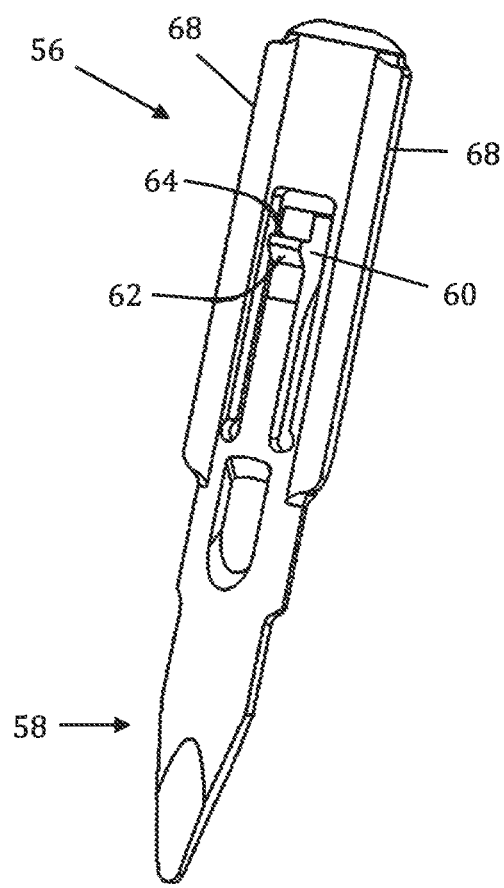
FIGS. 4-5 are front perspective and back perspective views, respectively, of one example of a locking shim forming part of the surgical access system of the present disclosure.
Figure 5:
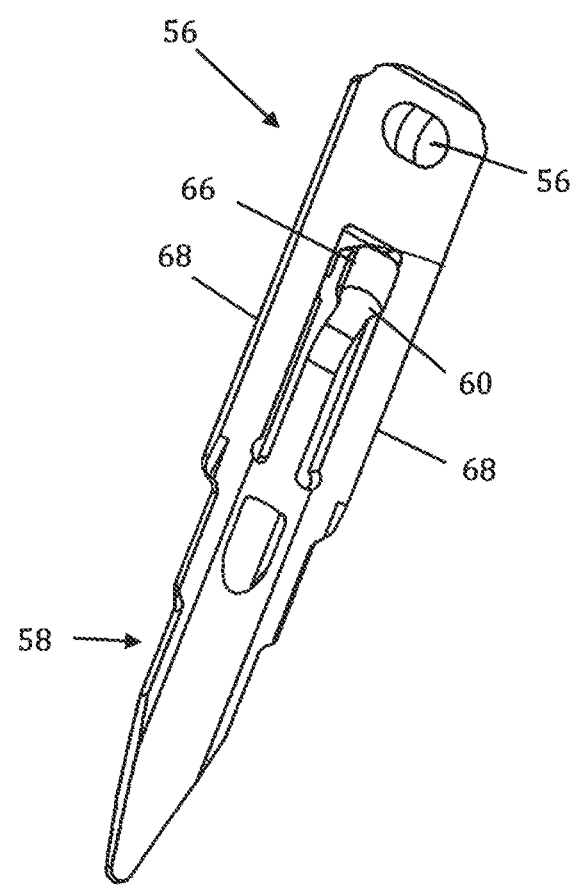
Figure 6:
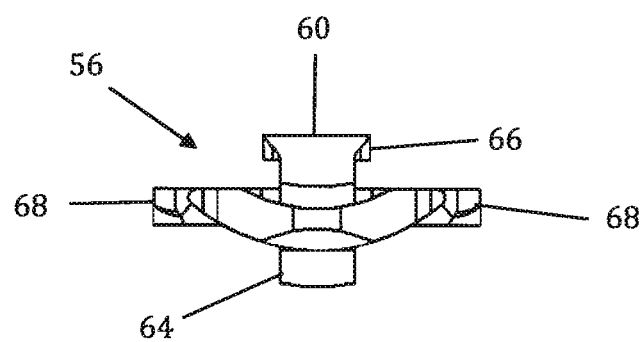
FIG. 6 is a top view of the locking shim of FIG. 4.
Figure 11:
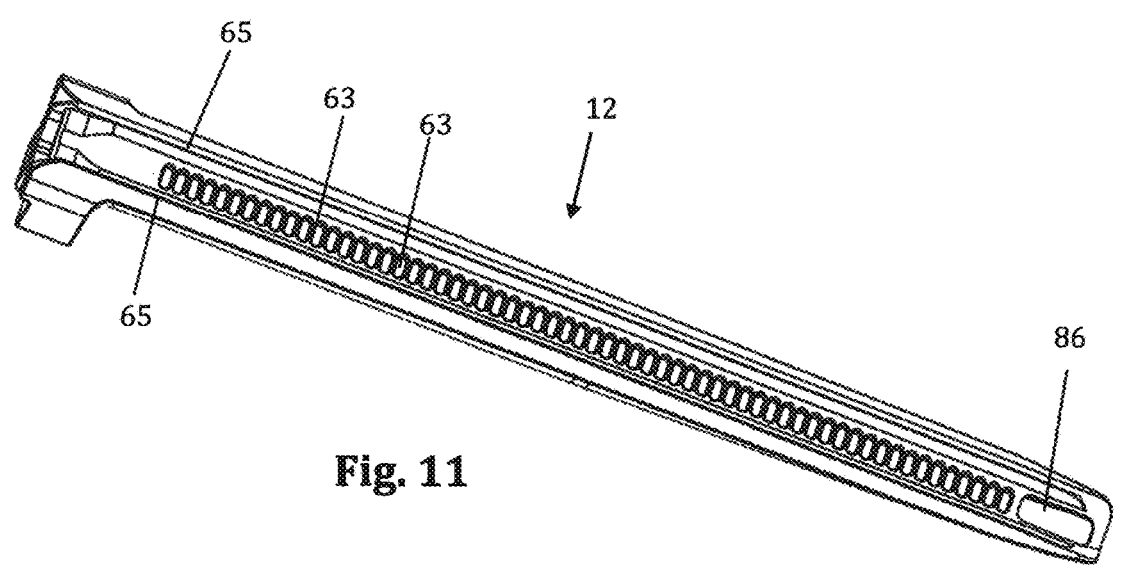
Figure 12:
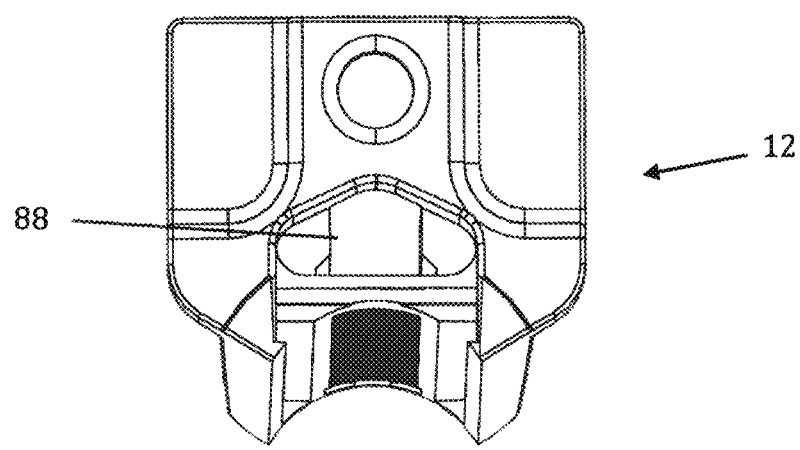
FIG. 12 is top perspective view of the retractor blade of FIG. 10.

The retractor blades 12, 16, 18 may be equipped with various additional features or components. By way of example only, one or more of the retractor blades 12, 16, 18 may be equipped with a shim, such as a locking shim 56 as shown in FIGS. 4-6. In a preferred embodiment, the intradiscal locking shim 56 is suitable for engagement with the posterior blade 12. However, it should be noted that any shim 56 may be used with any blade 12, 16, 18 without departing from the scope of the present disclosure. The locking intradiscal shim 56 has a distal tapered region 58 which may be advanced into the disc space for the purpose of distracting the adjacent vertebral bodies (thereby restoring disc height) and/or anchoring the blade 12 relative to the spine. The locking intradiscal shim 56 also forms a protective barrier to prevent the ingress or egress of instruments or biological structures (e.g. nerves, vasculature, etc.) into or out of the operative corridor 15. The locking intradiscal shim 56 locks in position on the retractor blade 12 to prevent the shim from dislodging and allowing the retractor to move from the targeted location. To lock position on the blade, the shim 56 has a flexible engagement tab 60 with a ramped leading edge 62 that allows it to advance down indentations 63 on the inner surface of the retractor blade 12 (FIG. 11). The trailing edge 64 of the engagement tab 60 is squared to prevent disengagement (thus preventing unwanted backout of the shim) from the indentation 63 without use of a removal tool (not shown). The engagement tab 60 also includes a T-shaped removal lip 66 configured to engage a shim removal tool, an example of which is shown and described in PCT App. No. PCT/US01/01489 (incorporated by reference). The T-shaped lip 66 of the engagement tab 60 allows the removal tool to lift the trailing edge 64 away from the retractor blade 12 and remove the shim 56. The locking intradiscal shim 56 has a pair of elongated tab members 68 that are configured to slideably engage elongated slot members 65 that run the length of the inside surface of the retractor blade 12 (FIG. 11). The locking intradiscal shim 56 includes a dimple or aperture 56 located near the proximal end of the shim 56 configured for engagement with a shim removal tool.

The locking intradiscal shim 56 may be made from any material suitable for use in the human body, including but not limited to biologically compatible plastic and/or metal, preferably partially or wholly radiolucent in nature material (such as aluminum, PEEK, carbon-fibers and titanium). The intradiscal shim 56 may also be coated with an insulative coating (e.g. a parylene coating) to prevent current shunting or density changes from electrodes situated at the distal end of the retractor blade 12. The shim element 56 may be composed of a material that would destruct when autoclaved (such as polymer containing a portion of glass particles), which may be advantageous in preventing the unauthorized re-use of the shim element 56 (which would be provided to the user in a sterile state).

According to the present disclosure, the locking intradiscal shim 56 may be provided with one or more electrodes (e.g. at or near their distal regions) equipped for use with a neuromonitoring system. Such a neuromonitoring system may be capable of detecting the existence of (and optionally the distance and/or direction to) neural structures during the retraction of tissue by detecting the presence of nerves by applying a stimulation signal to the electrodes and monitoring the evoked EMG signals from the myotomes associated with the nerves in the vicinity of the tissue retraction system 10 of the present disclosure. In so doing, the system as a whole (including the tissue retraction system 10 of the present disclosure) may be used to form an operative corridor through (or near) any of a variety of tissues having such neural structures, particularly those that, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

As mentioned above, a neuromonitoring system may be provided for use with the tissue retraction assembly. According to one example, the nerve monitoring component of the retractor system is the posterior retractor blade 12, which may be made of a conductive material (e.g. aluminum) and coated with a insulative coating to direct stimulation from the neuromonitoring system 17 to the tissue adjacent the distal end. According to another example embodiment, pictured in FIGS. 8-16, the nerve monitoring feature of the tissue retraction assembly includes two main components: a center (posterior) blade that forms part of a tissue retraction assembly 10 and an electrode body 70. For example, the electrode body 70 shown and described is slideably coupled to the posterior blade 12. By way of further example, the electrode body 70 shown is disposable. A clip cable 72 may be used to connect the electrode body 70 to the neuromonitoring system. One potential advantage of the electrode body 70 and accompanying posterior blade 12 is the increased ability to attain consistent and repeatable neuromonitoring functionality throughout the course of a single surgery and from surgery to surgery (since there is no risk of erosion of the insulative coating on the blade which can lead to current shunting).

Figure 7:
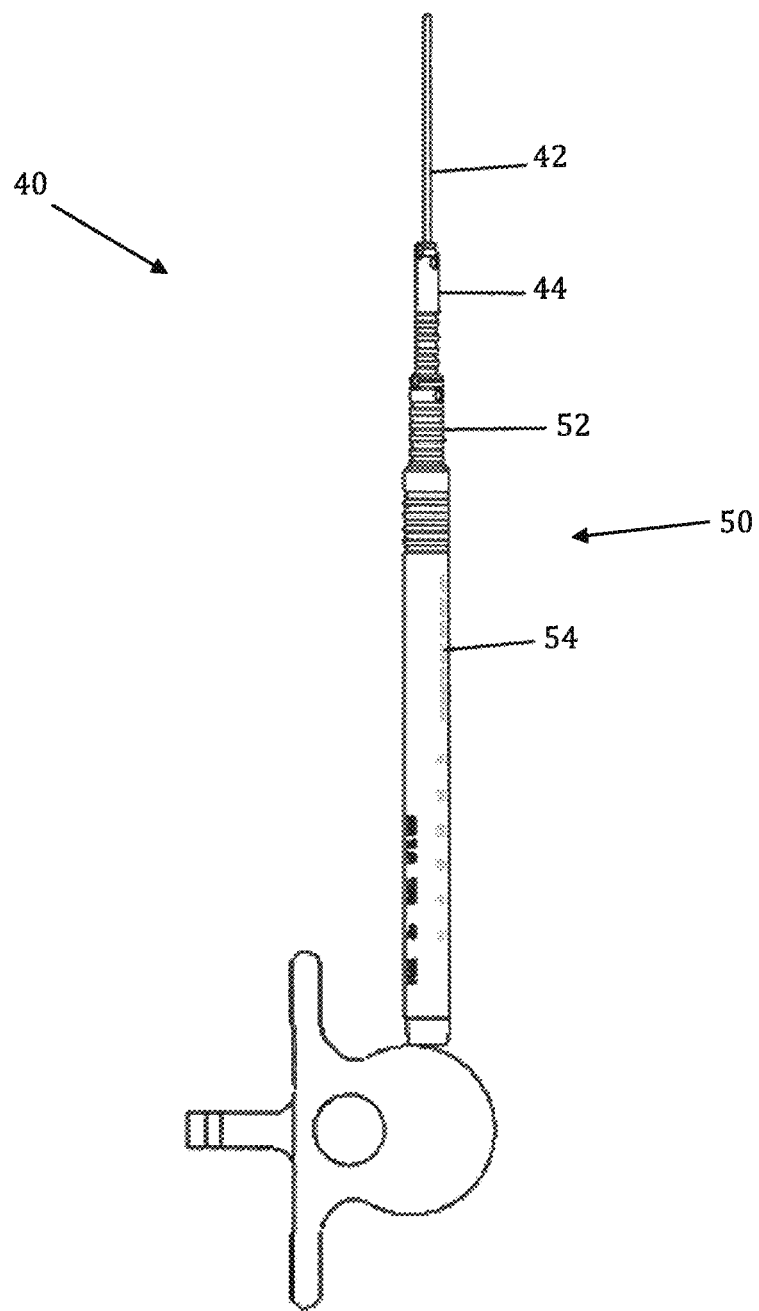
FIG. 7 is a side plan view of a tissue distraction assembly (comprising a plurality of dilating cannulae over a K-wire) used to distract tissue between the skin of the patient and the surgical target site according to one embodiment of the present disclosure.

FIG. 7 illustrates an example of a tissue distraction system 40 according to one embodiment. The tissue distraction system 40 includes a K-wire 42 and initial dilator 44, as well as a secondary dilation assembly 50. The secondary dilation assembly 50 includes at least two nesting cannulae 52, 54.

Figure 13:
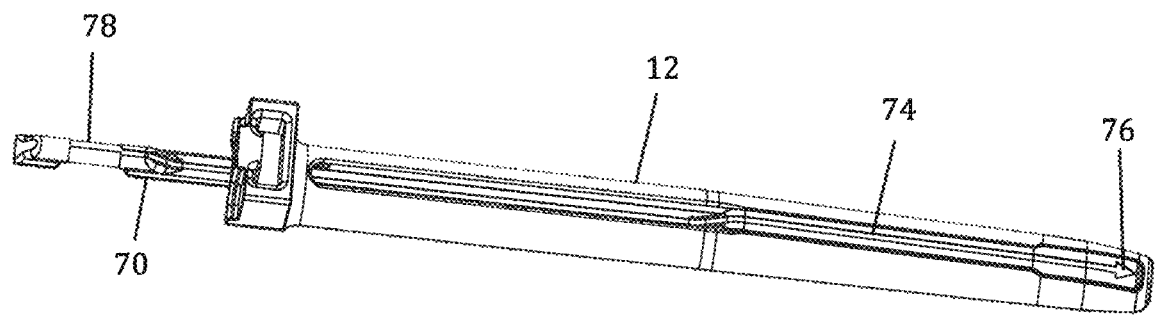
FIGS. 13-14 are perspective views of an assembly comprising the disposable electrode of FIG. 8 coupled to the retractor blade of FIG. 10.
Figure 14:
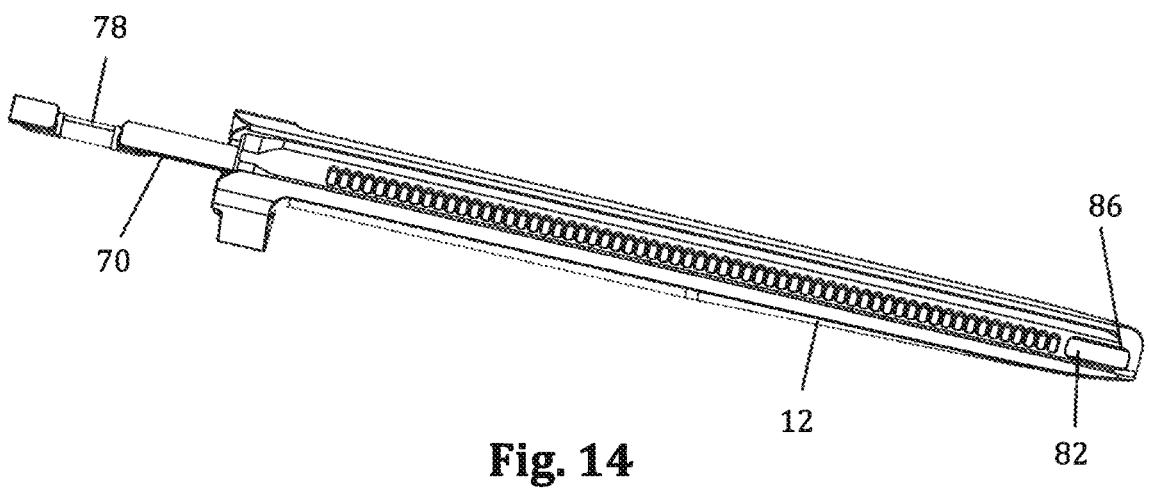
Figure 15:
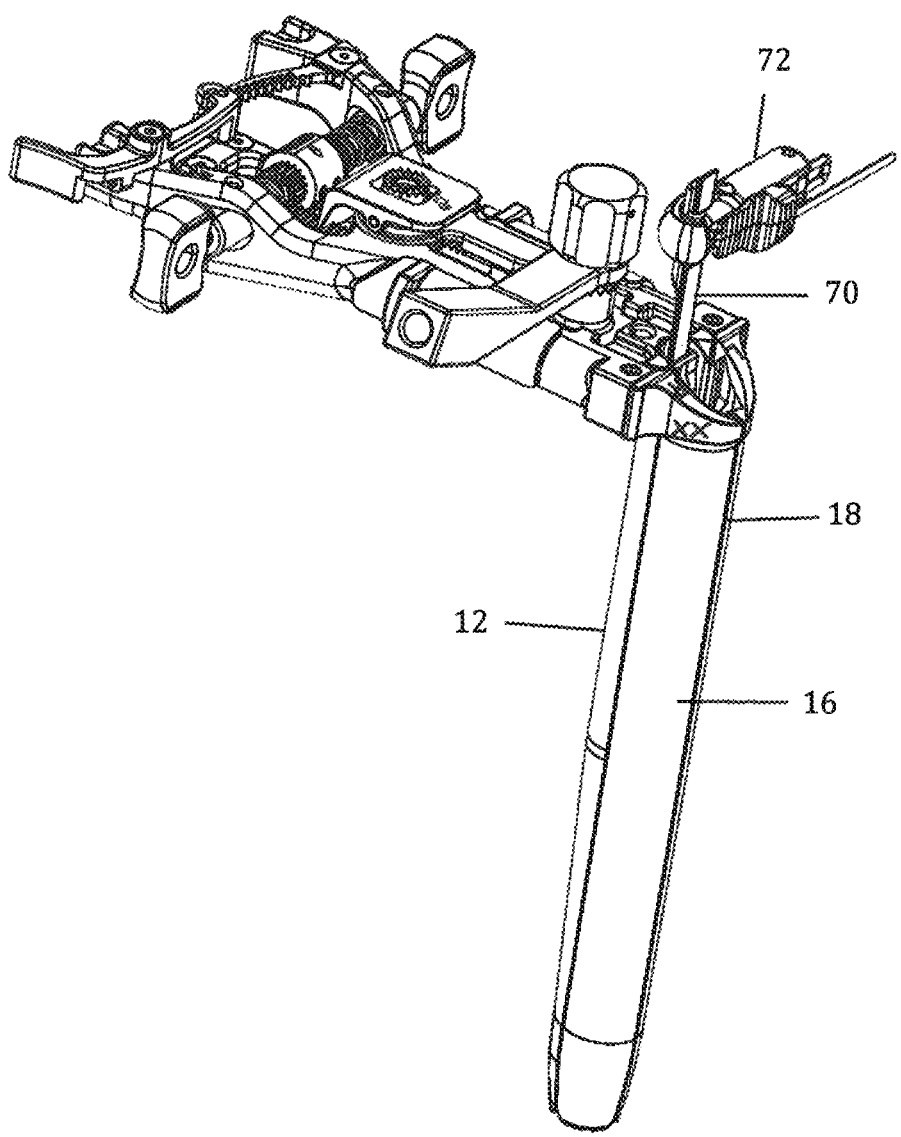
FIGS. 15-16 are perspective views of the tissue retraction assembly of FIG. 1 including the disposable electrode/blade assembly of FIG. 13.

FIGS. 8-16 illustrate an example of one embodiment of a removably couplable disposable electrode 70 and retractor blade 12 for use with the tissue retraction assembly 10 according to the present disclosure. The electrode 70 assists in the detection of the depth of nerves relative to the length of the posterior blade after the tissue retraction assembly is placed. The electrode 70 also assists in assessing the health and status of the nerves closest to the posterior blade 12 after the tissue retractor 10 is fully retracted in the open position and throughout the surgical procedure. (Open position refers to the level of retraction utilized to maintain the operative corridor to the spine during surgery.) Using a disposable electrode 70 permits the retractor blade 12 to be sterilized and reused endlessly without the possibility of degradation to the electrode. This in turn ensures that results from nerve monitoring using the electrode are consistent and reduces potentially high costs of replacing the entire blade structure if the electrode (or insulating regions surrounding the electrode) degrade. Although FIG. 15 illustrates the electrode 70 in use with only the posterior retractor blade 12, the electrode 70 could be used with each of the retractor blades 12, 16, and/or 18 without departing from the scope of this disclosure.

Figure 8:
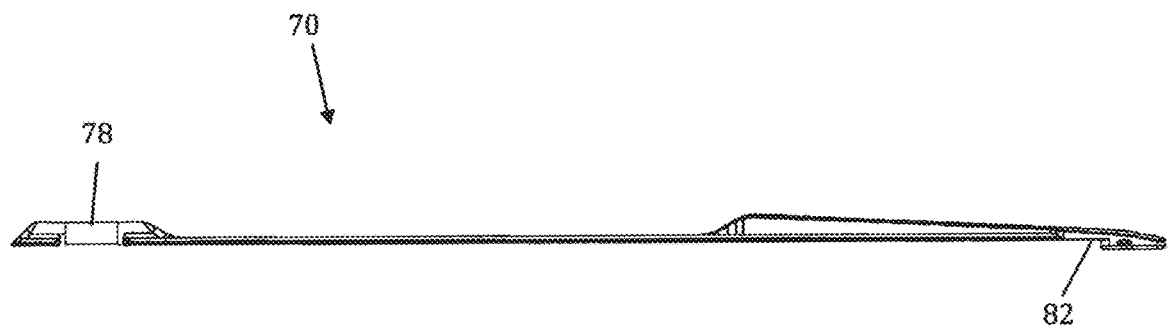
FIGS. 8-9 are side and perspective views, respectively, of an example of a disposable electrode forming part of the tissue retraction system of FIG. 1 according to one embodiment of the present disclosure.
Figure 9:
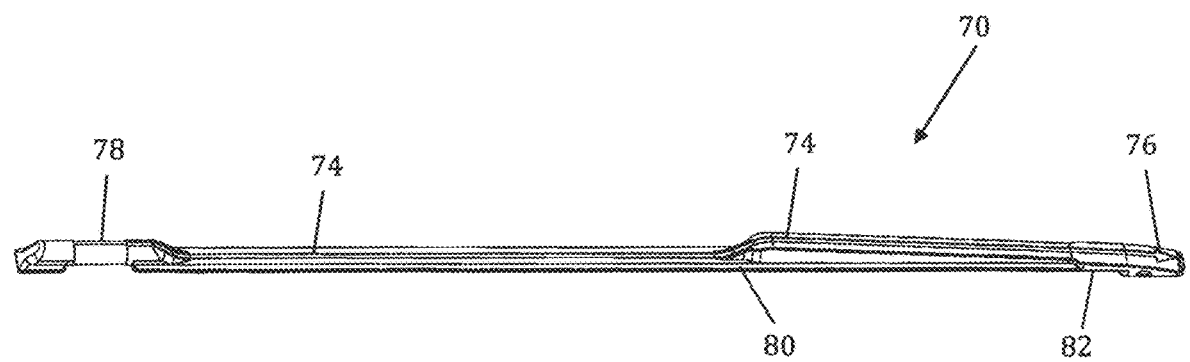
Figure 10:
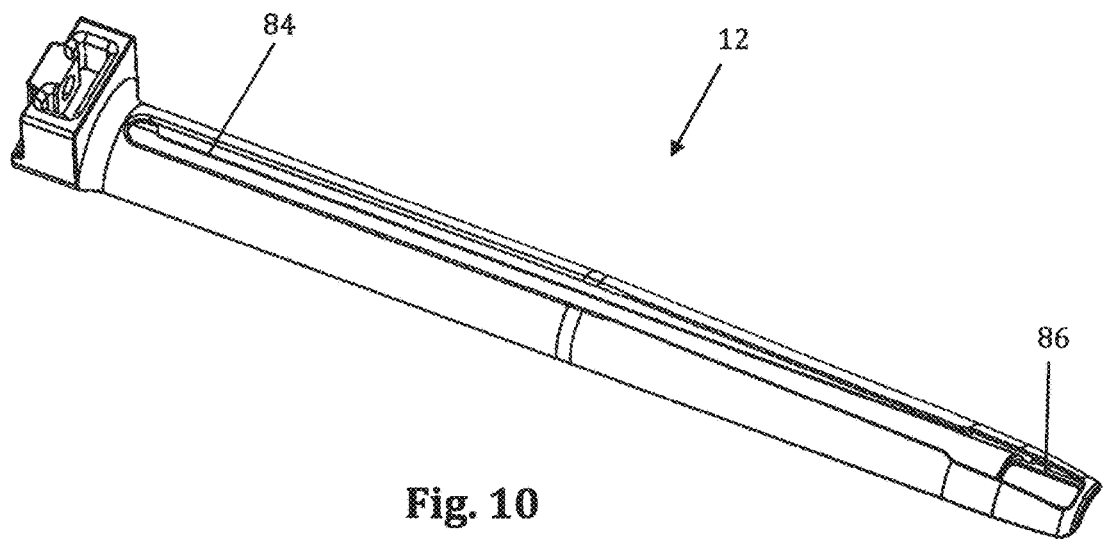
FIGS. 10-11 are perspective views of an example of a retractor blade forming part of the tissue retraction system of FIG. 1 configured to releasably couple with the disposable electrode of FIG. 9.

FIGS. 8-9 illustrate one example of an electrode 70 that includes a molded plastic part with a conductive trace 74 deposited generally along the length of the electrode 70. The conductive trace 74 may include a discrete trace for each electrode contact 76 on the electrode body 70. Preferably, the electrode 70 is made out of a generally stiff material that can also withstand bending without breaking, such as, for example, PVC. The conductive trace 74 provides a conductive pathway for the delivery of current from a current delivery source (such as a clip cable 72) to each electrode as well as for the delivery of electrical activity from nerve tissue at or near the surgical site to the neuromonitoring system. There are at least two areas along the electrode body 70 where the conductive trace 74 is exposed for enabling the delivery of current to and from the electrode 70. The proximal end of the electrode 70 has a first exposed area 78 that may wrap around the circumference of the proximal end of the electrode 70 to ensure a conductive path between the electrode 70 and a current delivery device or a current recording device (such as, for example, a clip cable 72). The first exposed area 78 can act as a stimulation conduit and allow a current delivery source to deliver an electric current to the conductive trace 74 and as a recording conduit that transmits changes in electrical current from the conductive trace 74 to the control unit 172 of the neuromonitoring system. The distal end of the electrode 70 has at least one electrode contact 76 (shown by way of example as a triangular patch) within the conductive trace 74 that can act as a stimulation conduit and allow the emitting of current to nearby tissue and as a recording conduit for recording changes in electrical current from nearby tissue. Both functions of the first exposed area 78 and distal electrode contact 76 will be explained in greater detail below. Other than the exposed areas 76, 78, the remainder of the conductive trace 74 is insulated with a dielectric coating to prevent current shunting. Any number of conductive materials suitable for completing the current pathway, such as, for example, silver, or copper may be used in the conductive trace 74 without departing from the scope of this disclosure.

Figure 16:
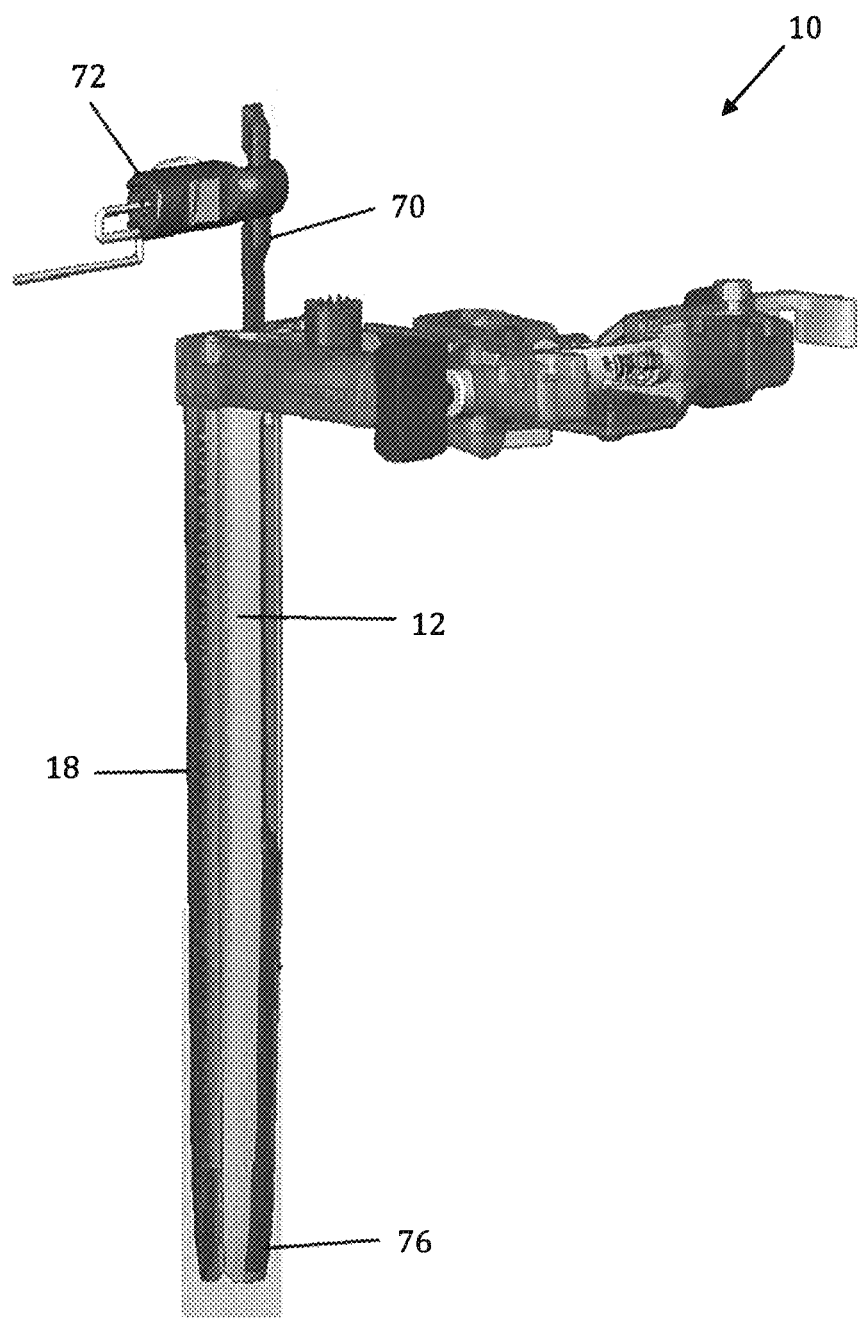

The first exposed area 78 of the disposable electrode may have a generally cylindrical shape for facilitating the connection between the electrode and a neuromonitoring system. For example, as shown in FIGS. 15-16, an electrical coupler is shown in the form of a plunger-style clip cable 72. Although shown as cylindrical, the connection site for a current delivery device or a current recording device (such as the clip cable 72) may be any size and shape necessary for making a quality electrical connection without departing from the scope of the current disclosure. The remainder of the body of the electrode 70 may be generally flat with minimal thickness and a variety of features for engaging and securing the electrode 70 to a retractor blade 12. For example, wings 80 may extend from the sides of the electrode 70 for engaging positioning features within the retractor blade 12, as will be discussed in more detail below. Additionally, the distal end of the electrode 70 may have a ledge 82 for engaging a feature of the retractor blade 12 for further secure positioning of the electrode 70 relative to the retractor blade 12, as will also be discussed in more detail below. A single sized electrode 70 may be designed for use with a variety of retractor blade 12 sizes and shapes (for example, retractor blade lengths generally ranging from 20 to 180 mm), but the electrodes may also be available in a variety of shapes and sizes.

FIGS. 13-14 illustrate one example assembly of an electrode 70 releasably coupled to retractor blade 12. Preferably, at least the posterior blade 12 is configured to enable the coupling of an electrode body 70. During assembly of the electrode body 70 to the retractor blade 12, the proximal end of the electrode 70 (more specifically, adjacent the first exposed area 78 end of the electrode 70) is inserted into generally the distal end of the retractor blade 12. The wings 80 of the electrode 70 mate with and are constrained by the dovetail grooves 84 which extend longitudinally from the distal end to the proximal end of the retractor blade 12. The dovetail grooves 84 provide an insertion guide for the disposable electrode 70 as it is inserted and assists in maintaining proper positioning of the electrode 70 while coupled to the retractor blade 12. Additionally, the ledge 82 near the distal end of the disposable electrode 70 may engage the cut-out 86 generally near the distal end of the retractor blade 12 to further assist in securing the positioning of the electrode 70 relative to the retractor blade 12. Therefore, the electrode 70 is adapted to the retractor blade 12 so that the electrode contact 76 (shown by way of example as triangular in FIGS. 9 and 13) is exposed generally along the outer surface of the blade (best shown in FIG. 13). Furthermore, the proximal end of the electrode body 70 protrudes from a machined cavity 88 (best shown in FIG. 12) at the proximal end of the retractor blade 12. Depending on the height of the blade, the proximal end may be bent or folded so as not to obstruct the surgical corridor.

Figure 17:
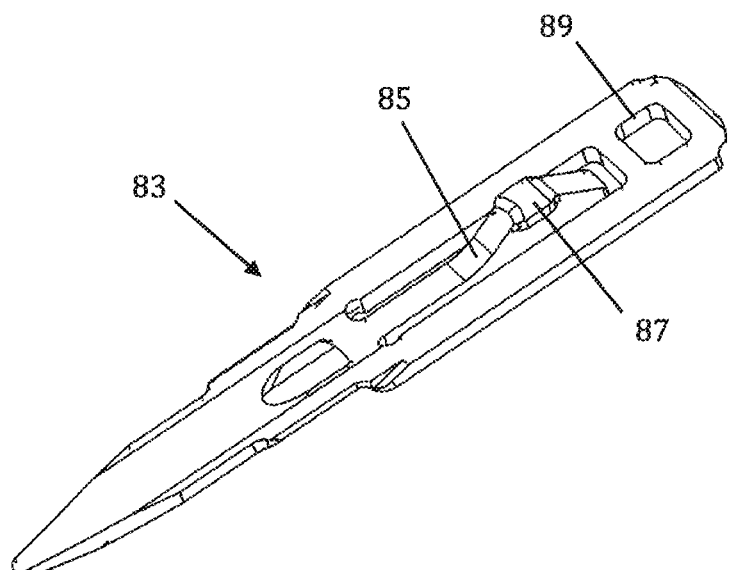
FIGS. 17-18 are perspective views of an example of an insulated locking shim for use with the posterior blade forming part of the tissue retraction system of FIG. 1 to prevent current shunting from the posterior blade when neurophysiologic monitoring is performed from the posterior blade.

FIG. 17 is illustrates a locking intradiscal shim 83 according to a second example embodiment. The locking intradiscal shim 83 is similar to the shim 56 of FIGS. 4-6 such that a description of all the like elements will not be repeated here. The locking intradiscal shim 83 of FIG. 17 is preferably coated with an insulative parylene coating to mitigate current shunting and changes to current density at the distal tip of the disposable electrode. Parylene is the trade name for a variety of chemical vapor deposited poly (p-xylylene) polymers used as moisture barriers and electrical insulators. Among such polymers, Parylene C is highly desirable due to its combination of barrier properties and manufacturing advantages. The locking intradiscal shim 83 includes a deflectable tab 85 with a lip member 87 that serves as a locking feature. The shim 83 further includes a cut-out 89 that receives an engagement tab of a removal tool.

Figure 18:
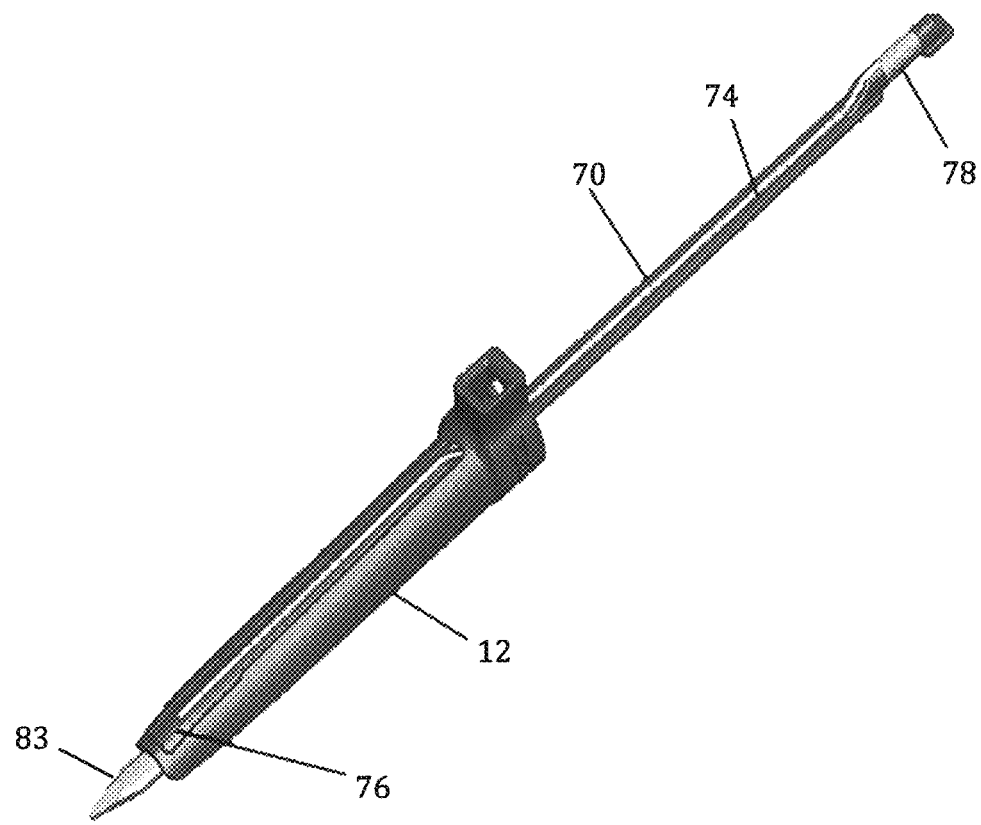

Any combination of the features described herein may be employed at any one time without departing from the scope of the present disclosure. For example, FIG. 18 illustrates the locking intradiscal shim 83 of FIG. 17 attached adjacent to the distal end of the disposable electrode 70 that is removably coupled to the posterior blade 12 described in relation to FIGS. 9-16 above. By coupling these several features, each of which include parylene coating to control shunting of electric current, better results can be achieved.

As mentioned above, any number of distraction components and/or retraction components (including but not limited to those described herein) may be equipped to detect the presence of (and optionally the distance and/or direction to) neural structures during tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Figure 19:
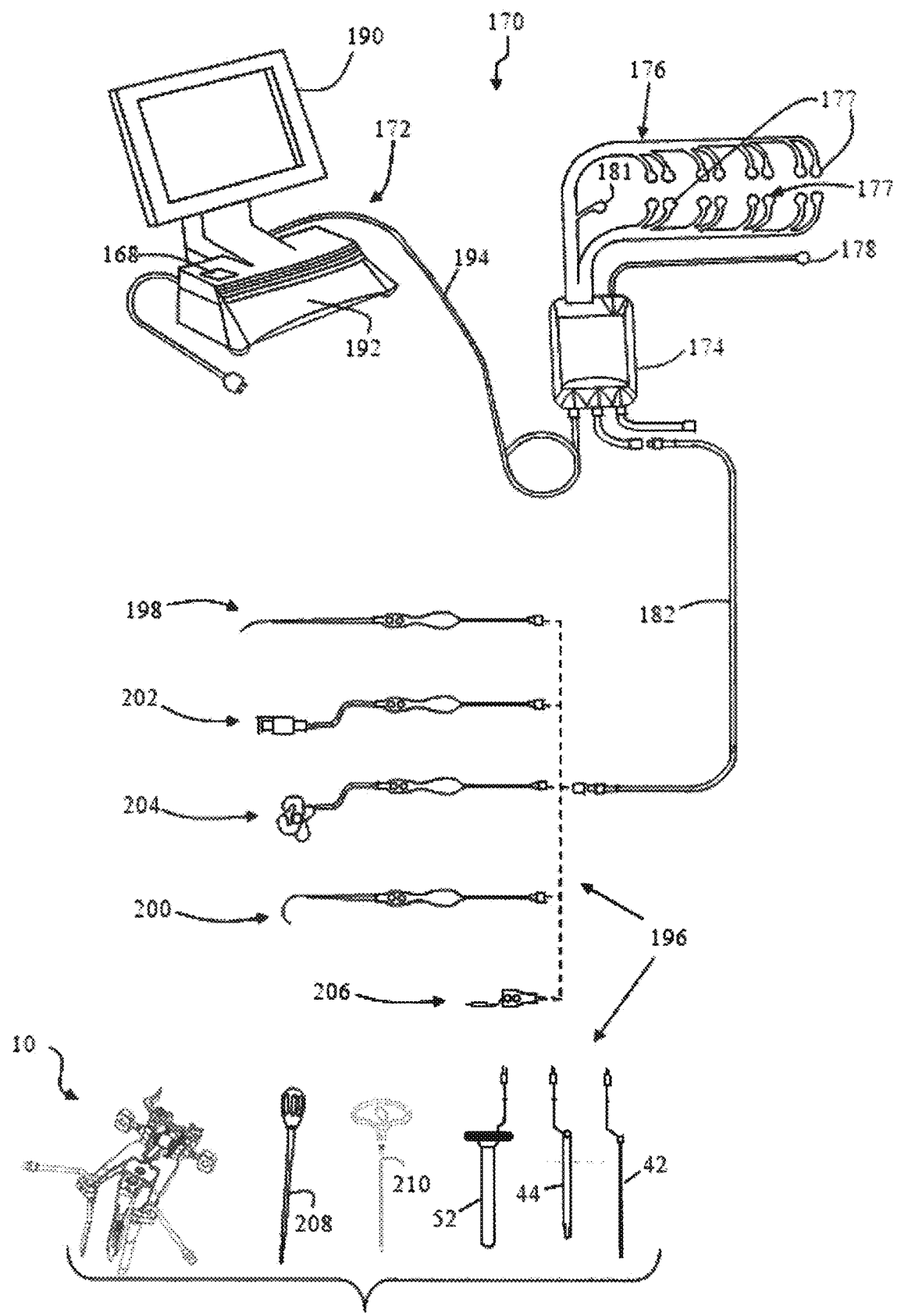
FIG. 19 is a perspective view of an example of a neuromonitoring system programmed to perform nerve monitoring before, during and after the creation of an operative corridor to a surgical target site in accordance with the present disclosure.
Figure 20:
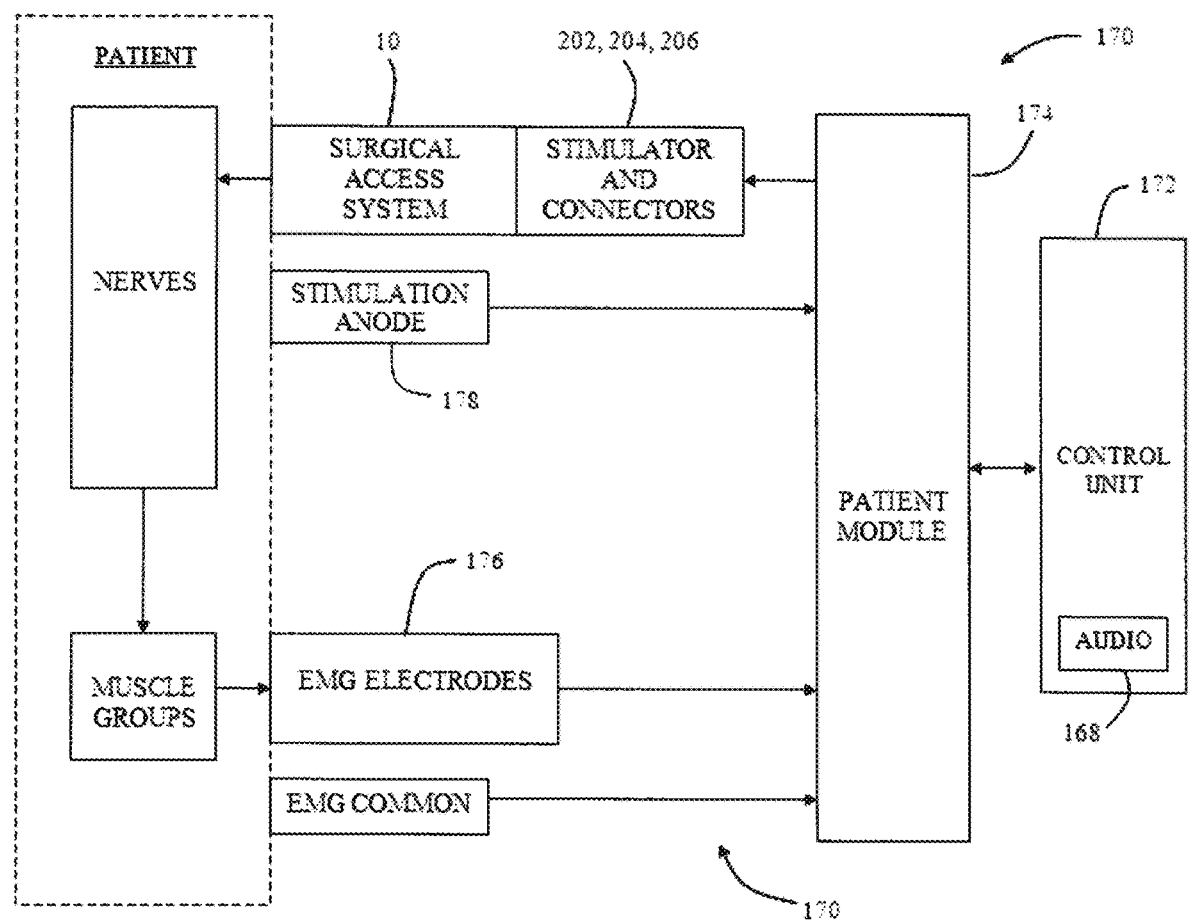
FIG. 20 is a block diagram of the neuromonitoring system shown in FIG. 19.

FIGS. 19-20 illustrate, by way of example only, a monitoring system 170 suitable for use with the surgical access system 10 of the present disclosure. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present disclosure (retractor assembly 10 of FIG. 1 and distraction assemblies 40, 50 of FIG. 7, including K-wire 42, initial dilator 44 and sequentially dilating cannulae 52, 54). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 44, 52, 54, the retractor blades 12, 16, 18, and/or the shim element 56 (collectively "surgical access instruments").

In order to use the monitoring system 170, then, these surgical access instruments must be connected to at least one of coupling devices 202, 204 (or similar couplers including multi-contact regions, not shown), at which point the user may selectively initiate a stimulation signal (preferably, a current signal) from the control unit 172 to a particular surgical access instruments. Stimulating the electrode(s) on these surgical access instruments before, during, and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the neuromonitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and neuromonitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the neuromonitoring system 170 is capable of determining nerve direction relative to one or more of the K-wire 42, the dilators 44, 52, 54, the retractor blades 12, 16, 18, and/or the shim element 56 before, during and/or following the creation of an operative corridor to a surgical target site. Neuromonitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 21:
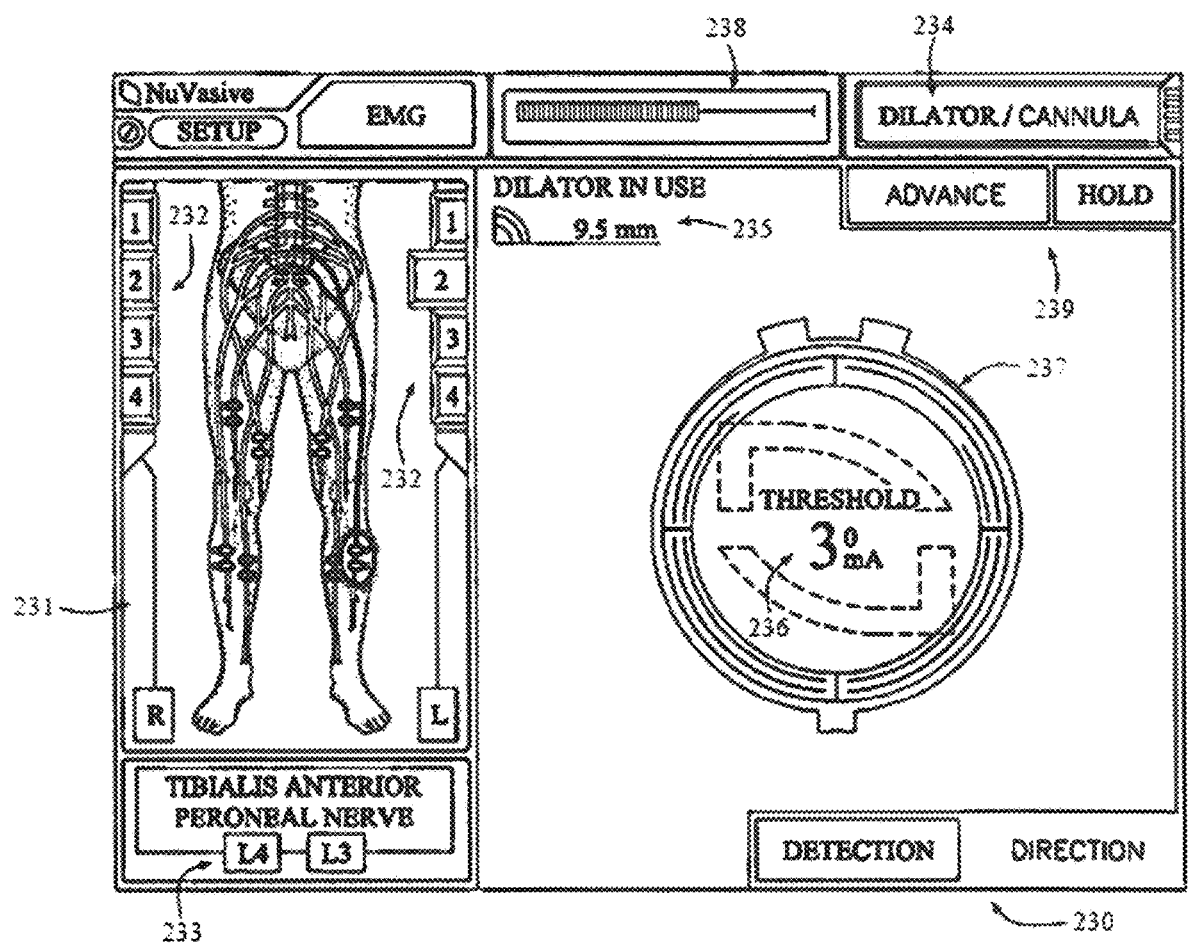
FIGS. 21-22 are examples of screen displays illustrating exemplary features and information communicated to a user during the use of the neuromonitoring system of FIG. 19.
Figure 22:
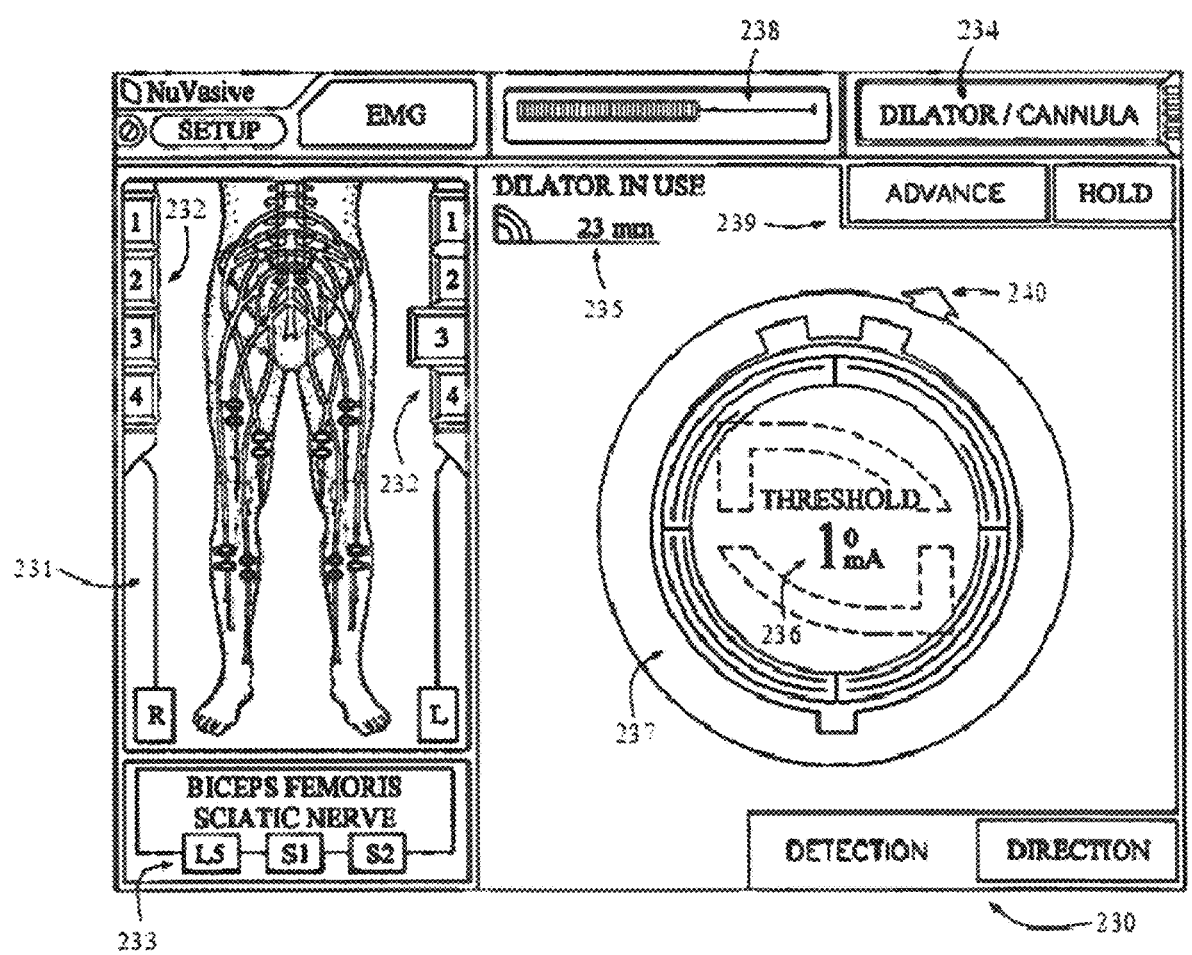

FIGS. 21-22 are exemplary screen displays (to be shown on the display 190) illustrating one embodiment of the nerve direction feature of the neuromonitoring system 170 shown and described with reference to FIG. 19-20. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator 52, 54), the size of the instrument being used 235, the stimulation threshold current 236, a graphical representation of the instrument being used 237 (in this case, a cross-sectional view of a dilator 52, 54) to provide a reference point from which to illustrate relative direction of the instrument to the nerve, the stimulation current being applied to the stimulation electrodes 238, instructions for the user 239 (in this case, "ADVANCE" and/or "HOLD"), and an arrow 240 indicating the direction from the instrument to a nerve. This information may be communicated in any number of suitable fashions, including but not limited to the use of visual indicia (such as alphanumeric characters, light-emitting elements, and/or graphics) and audio communications (such as a speaker element). Although shown with specific reference to a dilating cannula (such as at 234), it is to be readily appreciated that the present disclosure is deemed to include providing similar information on the display 190 during the use of any or all of the various instruments forming the surgical access system 10 of the present disclosure, including the distraction assembly 40 (i.e. the K-wire 42 and dilators 44, 52, 54) and/or the retractor blades 12, 16, 18 and/or the shim element 56.

According to another broad aspect of the present disclosure, there is provided a method for monitoring the status of the motor neural pathway that includes the steps of: (a) stimulating the motor pathways in a transcutaneous and trans-abdominal fashion from a location superior to the surgical site and (b) recording neurophysiologic responses evoked by that transcutaneous, trans-abdominal stimulation from one or more locations inferior to the surgical site.

The neuromonitoring system 170 is capable of ascertaining the health and/or status of at-risk nerves along the motor neural pathway superior and inferior to the surgical site before, during, and/or after the creation of the operative corridor to the surgical target site. Monitoring system 170 accomplishes this by having the control unit 172 and patient module 174 cooperate to transmit electrical stimulation signals to a stimulating cathode placed posteriorly on the patient's lower back above the site of surgery. The stimulation signals cause nerves deep to the stimulating electrode to depolarize, evoking activity from muscles innervated by the nerves. Evoked EMG responses of the muscles are recorded by the neuromonitoring system 170 and analyzed in relation to the stimulation signal (discussed below). Resulting data from the analysis is conveyed to the surgeon on the GUI display. This provides the ability to verify that the patient is positioned in a neutral way and that no neural structures have been impinged upon after the operative corridor has been established. In spinal surgery, for example, this is particularly advantageous in that the surgical access system 10 may be particularly suited for establishing an operative corridor to an intervertebral target site in a posterolateral, trans-psoas fashion so as to avoid the bony posterior elements of the spinal column.

Figure 23:
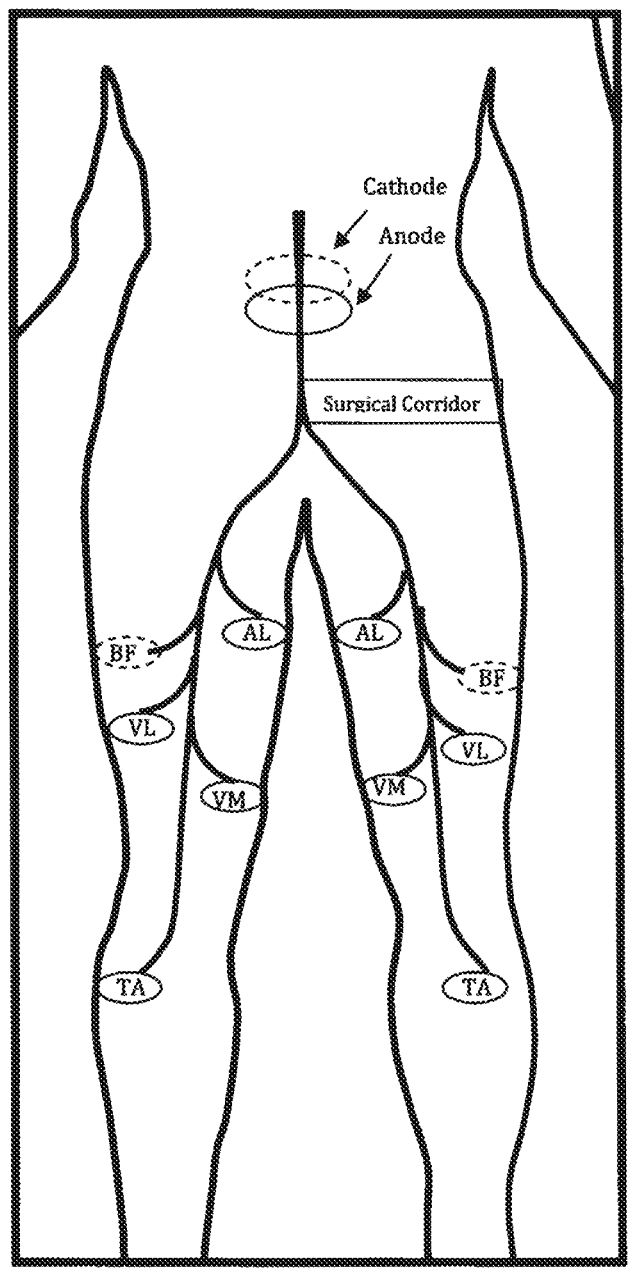
FIG. 23 is a partial diagram of a patient depicting an example electrode placement pattern required for performing transcutaneous, trans-abdominal nerve root stimulation.

In one implementation, a stimulating cathode is placed posteriorly and an anode is placed anteriorly at locations superior to the surgical target site and neuromuscular responses are evoked in response to transcutaneous, trans-abdominal nerve root stimulation. By way of example only, the stimulating cathode may be a single cathode adhesive surface electrode placed over the conus medullaris at spinal level L1-2, preferably with the electrode pair oriented side to side and symmetrically over the neural foramen. The anode electrode may be an adhesive surface electrode placed at the anterior abdominal midline below the umbilicus, preferably with the electrode pair oriented side to side, symmetrically across the midline. Implementing a stimulation montage in this way is beneficial for at least two reasons. First, stimulating trans-abdominally does not evoke muscle twitching of the head, upper extremities, or upper torso which leads to less patient movement. Second, using a surface electrode with a larger surface electrode anteriorly and a smaller surface electrode posteriorly may decrease the current density travelling trans-abdominally, reducing the depolarization of the abdominal muscles and thus, further decreasing the amount of patient movement. Recording electrodes may be placed on or in muscles innervated by one or more nerves of the lumbar plexus. Electrode harness 176 may be designed such that the various electrodes may be positioned about the patient as described in Table 1 and shown in FIG. 23 (depicting an example electrode placement diagram indicating electrodes placed on the anterior portion of the body with solid lines and electrodes placed on the posterior portion of the body with dashed lines).

TABLE 1

| Electrode Type | Electrode Placement | Spinal Level |
|---|---|---|
| Ground | Upper Outer Thigh | — |
| Anode | Abdominal Midline, Below Umbilicus | — |
| Stimulation | Lower Back, over Spinal Level 1-2 | — |
| Recording | Left Adductor Longus | L2, L3, L4 |
| Recording | Left Vastus Medialis | L2, L3, L4 |
| Recording | Left Vastus Lateralis | L2, L3, L4 |
| Recording | Left Tibialis Anterior | L4, L5 |
| Recording | Left Biceps Femoris | L5, S1, S2 |
| Recording | Right Adductor Longus | L2, L3, L4 |
| Recording | Right Vastus Medialis | L2, L3, L4 |
| Recording | Right Vastus Lateralis | L2, L3, L4 |
| Recording | Right Tibialis Anterior | L4, L5 |
| Recording | Right Biceps Femoris | L5, S1, S2 |

A basic premise underlying the methods employed by the system 170 for transcutaneous, trans-abdominal nerve root stimulation (as well as any other nerve monitoring functions conducted by the system 170) is that nerves have characteristic threshold current levels at which they will depolarize, resulting in detectable muscle activity. Below this threshold current, stimulation signals will not evoke a significant EMG response. Determinations of stimulation threshold may be made using a linear or non-linear hunting algorithm, such as for example for example the threshold hunting algorithm or algorithms described in the above-referenced '045 patent (incorporated by reference).

The steps of performing transcutaneous, trans-abdominal stimulation and recording the resultant evoked potentials is preferably first performed prior to establishing the lateral access corridor and subsequently performed periodically during the surgical procedure. In this way, the neuromonitoring system 170 is capable of detecting changes to the stimulation threshold intensities of these nerves over time which may be indicative of changes to the health/status of these nerves (e.g. by compression or patient positioning). By way of example only, a change in the health or status of a nerve may be deemed significant once the stimulus intensity required to elicit a neuromuscular response from a myotome exceeds pre-determined criteria (e.g. 50 mA greater than the baseline stimulation threshold). The neuromonitoring system 170 may quickly and accurately determine this data and convey the useful information in a simple and easily comprehensible manner for interpretation by a surgeon, neurophysiologist, or other medical personnel. It is contemplated that the control unit 172 of the neuromonitoring system 170 may automatically ascertain this information and/or communicate any of numerical, graphic, audio, and visual feedback corresponding to one or more of these findings. Armed with this useful information, the surgeon may detect a problem or potential problem early and then act to avoid and/or mitigate the problem.

Figure 24:
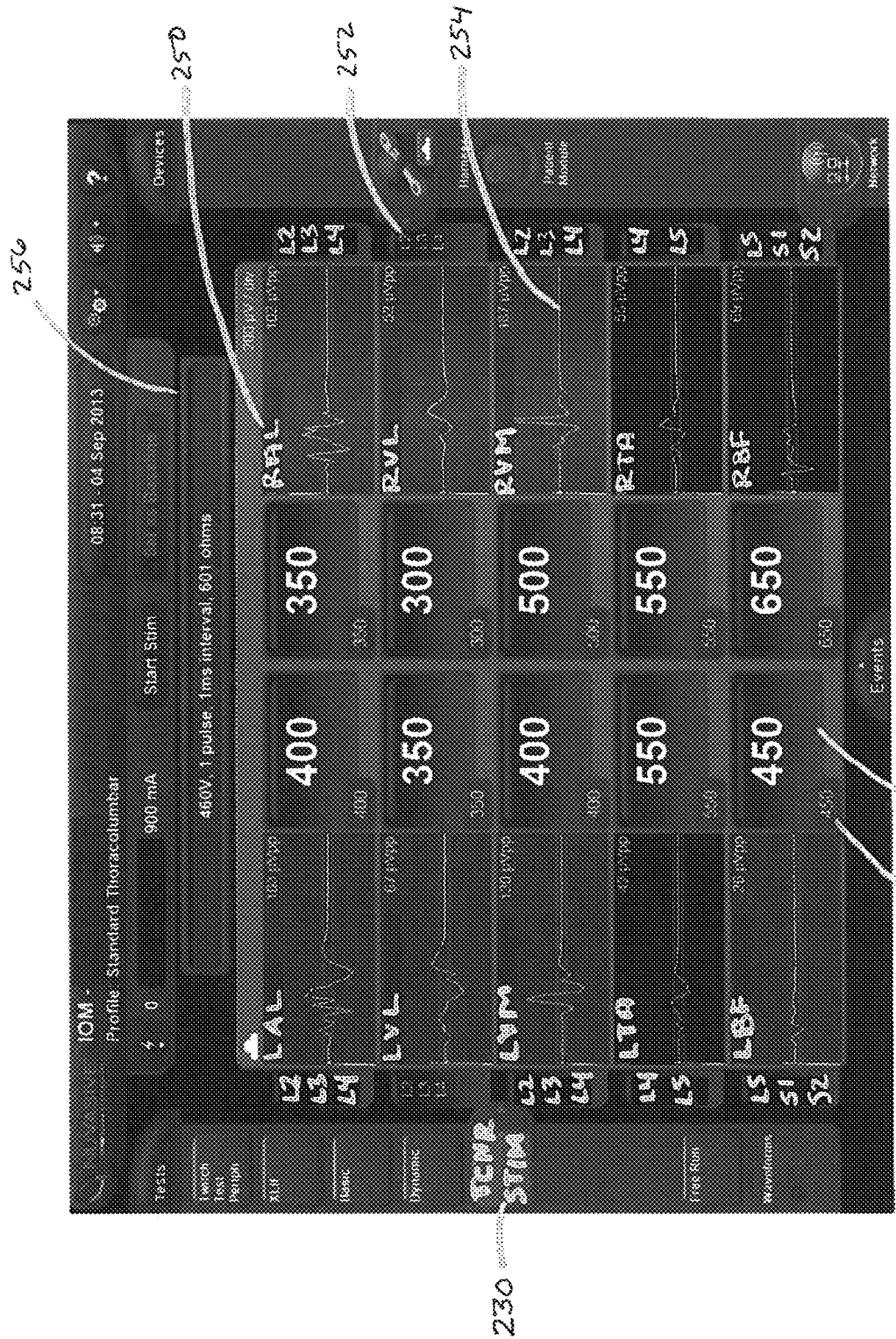
FIG. 24 is an example screen display illustrating exemplary features and information communicated to a user during the use of the neuromonitoring system of FIG. 19 using the transcutaneous, trans-abdominal nerve root stimulation feature in accordance with the present disclosure.

FIG. 24 is an exemplary screen display (to be shown on the display 190) illustrating one embodiment of the transcutaneous, trans-abdominal nerve root stimulation feature of the neuromonitoring system 170 shown and described with reference to FIGS. 19-20. These screen displays are intended to communicate information to the surgeon or other personnel in an easy-to-interpret fashion. This information may include, but is not necessarily limited to, a display of the function 230 (in this case "TCNR Stim"), the spinal levels being monitored 250, the nerve or group of nerves associated with the spinal levels being monitored 252, waveforms of the evoked EMG responses 254, stimulation parameters 256, the stimulation intensity required to elicit a response 258, and the stimulation intensity required to elicit a baseline (threshold) response 260. This information may be communicated in any number of suitable fashions, including but not limited to, the use of visual indicia (such as alpha-numeric characters, light-emitting element, and/or graphics) and audio communications (such as a speaker element).

Any combination of the nerve monitoring methods described herein may be employed at any one time without departing from the scope of the present disclosure. For example, the transcutaneous, trans-abdominal nerve root stimulation method described herein may be used in conjunction with the monitoring method described above during surgical access with a surgical access system.

As evident from the above discussion and drawings, the present disclosure accomplishes the goal of performing nerve monitoring in the tissue or regions superior and/or inferior to the surgical target site during any procedures performed after the operative corridor has been established and does so in a manner that lowers the amount of stimulation delivered to the patient and provides specificity of the at-risk nerve or nerves. While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the disclosure is to cover all modifications, equivalents, and alternatives falling within the spirit and scope of the disclosure as defined herein. For example, any of the features of a particular example described herein may be used with any other example described herein without departing from the scope of the present disclosure.

What is claimed is:

1. A method for a spinal surgical procedure, the method comprising:
    adhering a cathode electrode to skin of a patient such that the cathode electrode is positioned posteriorly on the patient with the cathode electrode at spinal level L1-L2 and superior to a surgical target site;
    adhering an anode electrode to the skin of the patient such that the anode electrode is positioned anteriorly on the patient with the cathode electrode on the patient's abdominal midline superior to the surgical target site;
    adhering a first recording electrode of one or more recording electrodes at a muscle innervated by one or more nerves of the patient's lumbar plexus;
    during the spinal surgical procedure and before forming an incision as part of creating an operative corridor, delivering, from the posteriorly adhered cathode electrode at spinal level L1-L2 superior to the surgical target site to the anteriorly adhered anode electrode on the patient's abdominal midline superior to the surgical target site, one or more initial transcutaneous, trans-abdominal stimulation signals to the patient selected to cause muscle activity inferior to the surgical target site detectable by one or more of the one or more recording electrodes;
    determining an initial stimulation threshold intensity required to elicit at least one neuromuscular response with at least one of the one or more initial transcutaneous, trans-abdominal stimulation signals, the at least one neuromuscular response detected via the one or more recording electrodes;
    after determining the initial stimulation threshold intensity, creating a lateral trans-psoas operative corridor to the surgical target site, wherein creating the operative corridor includes forming an incision;
    during or after creating the operative corridor:
        inserting at least one retractor blade of a tissue retraction assembly through the incision into the operative corridor;
        providing electrical stimulation with at least one electrode disposed on the at least one retractor blade;
        based on a response to the electrical stimulation provided with the at least one electrode on the at least one retractor blade, determining neural structures nearby the at least one retractor blade;
        delivering, from the posteriorly adhered cathode electrode at spinal level L1-L2 superior to a surgical target site to the anteriorly adhered anode electrode on the patient's abdominal midline at a lumbar spinal level superior to the surgical target site, one or more subsequent transcutaneous, trans-abdominal stimulation signals through the patient that are selected to cause detectable muscle activity inferior to the surgical target site;
        determining a subsequent stimulation threshold intensity required to elicit at least one neuromuscular response with at least one of the one or more subsequent transcutaneous, trans-abdominal stimulation signals, the at least one neuromuscular response detected via one or more recording electrodes positioned on the patient at a location inferior to the surgical target site; and
        determining nerve health during the spinal surgical procedure based on a comparison of the determined initial stimulation threshold intensity and the subsequent stimulation threshold intensity required to elicit at least one neuromuscular response prior to establishment of the operative corridor; and
    providing one or more instructions to display the determined nerve health during the spinal surgical procedure via a display.

2. The method of claim 1, wherein delivering the one or more initial transcutaneous, trans-abdominal stimulation signals to the patient's spine includes increasing a stimulation current associated with the one or more transcutaneous, trans-abdominal stimulation signal until the at least one neuromuscular response is elicited.

3. The method of claim 1, wherein determining the stimulation threshold intensity includes using one of a linear and a non-linear hunting algorithm.

4. The method of claim 1, wherein each transcutaneous, trans-abdominal stimulation signal of the one or more intial transcutaneous, trans-abdominal stimulation signals is a single pulse signal.

5. The method of claim 1, further comprising:
    adhering a second electrode of the one or more recording electrodes proximate an adductor longus of the patient;
    adhering a third electrode of the one or more recording electrodes proximate a vastus medialis of the patient; and
    adhering a fourth electrode of the one or more recording electrodes proximate a vastus lateralis of the patient.

6. The method of claim 1, wherein determining the nerve health during the spinal surgical procedure based on a comparison of the determined initial stimulation threshold intensity and the subsequent stimulation threshold intensity required to elicit at least one neuromuscular response prior to establishment of the operative corridor includes:
- determining significance of the nerve health responsive to determining that the subsequent stimulation threshold intensity is at least 50 mA greater than the initial stimulation threshold.

7. The method of claim 1, wherein determining the nerve health includes determining an effect of intraoperative nerve compression or patient positioning on the health of the nerves.

8. The method of claim 1, further comprising:
- passing an implant through the operative corridor to the surgical target site.

9. The method of claim 1, further comprising:
- providing one or more instructions to cause the display to present:
  - one or more visual indicia indicating that transabdominal nerve root stimulation mode is active;
  - one or more visual indicia indicating spinal levels being monitored;
  - one or more visual indicia indicating a nerve or group of nerves associated with the spinal levels being monitored;
  - waveforms of evoked neuromuscular responses;
  - one or more visual indicia indicating stimulation parameters;
  - one or more visual indicia indicating stimulation intensity required to elicit a response; and
  - one or more visual indicia indicating a stimulation intensity required to elicit a threshold response.

10. The method of claim 1, further comprising:
- establishing an electrical connection with a pedicle screw test probe; and
- performing pedicle screw tests with the pedicle screw test probe.

11. The method of claim 1, wherein the cathode electrode is adhered on the patient's abdominal midline entirely below the patient's umbilicus.

12. The method of claim 1, further comprising:
- during or after creating the operative corridor, completing deployment of the tissue retraction assembly,
- wherein delivering the one or more subsequent transcutaneous, trans-abdominal stimulation signals is performed after completing placement of the tissue retraction assembly.

13. The method of claim 1,
- wherein delivering the one or more subsequent transcutaneous, trans-abdominal stimulation signals is performed after creating the operative corridor.

14. The method of claim 1, further comprising:
- applying a ground electrode to the patient's thigh.

15. The method of claim 1, further comprising:
- applying at least ten recording electrodes to the patient.

16. The method of claim 1, further comprising:
- applying a common electrode to the patient that provides a ground reference.

17. The method of claim 1, wherein the anode electrode has a larger surface area than the cathode electrode.

* * * * *